US012758800B2

(12) United States Patent
Ko et al.

(10) Patent No.: US 12,758,800 B2
(45) Date of Patent: Oct. 13, 2026

(54) SKIN TREATMENT APPARATUS USING HIGH-INTENSITY FOCUSED ULTRASOUND, CONTROL METHOD THEREOF, AND SKIN TREATMENT METHOD USING THE SAME

(71) Applicant: LUTRONIC CORPORATION, Goyang-si (KR)

(72) Inventors: Kwangchon Ko, Paju-si (KR); Jaewon Choi, Seoul (KR)

(73) Assignee: LUTRONIC CORPORATION, Goyang-si (KR)

( * ) Notice: Subject to any disclaimer, the term of this patent is extended or adjusted under 35 U.S.C. 154(b) by 277 days.

(21) Appl. No.: 17/911,969

(22) PCT Filed: Dec. 21, 2021

(86) PCT No.: PCT/KR2021/019524

§ 371 (c)(1),
(2) Date: Apr. 20, 2023

(87) PCT Pub. No.: WO2023/063494

PCT Pub. Date: Apr. 20, 2023

(65) Prior Publication Data

US 2024/0207655 A1 Jun. 27, 2024

(30) Foreign Application Priority Data

Oct. 15, 2021 (KR) ........................ 10-2021-0137667
Oct. 15, 2021 (KR) ........................ 10-2021-0137668

(51) Int. Cl.
*A61N 7/02* (2006.01)
*A61N 1/06* (2006.01)
(Continued)

(52) U.S. Cl.
CPC ................. *A61N 7/02* (2013.01); *A61N 1/06* (2013.01); *A61N 1/328* (2013.01); *A61N 2007/0034* (2013.01)

(58) Field of Classification Search
CPC . A61N 7/00; A61N 1/328; A61N 1/06; A61N 2007/0034
See application file for complete search history.

(56) References Cited

U.S. PATENT DOCUMENTS 7,955,262 B2 6/2011 Rosenberg
8,702,769 B2 4/2014 Eckhouse
(Continued)

FOREIGN PATENT DOCUMENTS

KR 10-1226659 B1 2/2013
KR 10-1246557 B1 3/2013
(Continued)

OTHER PUBLICATIONS

The Extended European Search Report for European Patent Application No. 21931931.6, dated Mar. 6, 2024.

*Primary Examiner* — Pascal M Bui Pho

(57) ABSTRACT

The skin treatment apparatus using high-intensity focused ultrasound according to the disclosure, the control method thereof, and the skin treatment method using the same, it is possible to shorten treatment time because a wide area is first heated and a target position is then heated to be remodeled when tissue is heated. Further, it is possible to have an improved recovering effect because activity of cells is enhanced. Further, it is possible to have effects on securing operation stability because a transducer is movable by magnetic force while environments inside a cartridge are independently maintained.

13 Claims, 28 Drawing Sheets

(51) Int. Cl.
*A61N 1/32* (2006.01)
*A61N 7/00* (2006.01)

(56) References Cited

U.S. PATENT DOCUMENTS

| | | | | |
|---|---|---|---|---|
| 2007/0077230 | A1* | 4/2007 | Mon | A61B 18/1477 514/44 R |
| 2007/0239075 | A1* | 10/2007 | Rosenberg | A61N 1/328 601/2 |
| 2008/0221491 | A1* | 9/2008 | Slayton | A61N 7/00 601/3 |
| 2011/0213279 | A1* | 9/2011 | Britva | A61N 7/00 601/2 |
| 2013/0046209 | A1 | 2/2013 | Slayton | |
| 2018/0154185 | A1* | 6/2018 | Kim | A61N 7/00 |
| 2020/0086145 | A1* | 3/2020 | Yoo | A61B 90/03 |
| 2021/0146119 | A1* | 5/2021 | Prouza | A61N 5/0616 |
| 2021/0393992 | A1* | 12/2021 | Ji | A61N 1/08 |

FOREIGN PATENT DOCUMENTS

| | | | |
|---|---|---|---|
| KR | 101700334 | B1 | 1/2017 |
| KR | 10-1784536 | B1 | 11/2017 |
| KR | 10-2020-0042294 | A | 4/2020 |
| KR | 10-2020-0105104 | A | 9/2020 |

* cited by examiner

SKIN TREATMENT APPARATUS USING HIGH-INTENSITY FOCUSED ULTRASOUND, CONTROL METHOD THEREOF, AND SKIN TREATMENT METHOD USING THE SAME

TECHNICAL FIELD

This application is based on and claims priority under 35 U.S.C. § 119 to Korean Patent Application No. 10-2021-0137667 filed on Oct. 15, 2021 and No. 10-2021-0137668 filed on Oct. 15, 2021 in the Korean Intellectual Property Office, the disclosure of which is incorporated by reference herein in its entirety.

The disclosure relates to a skin treatment apparatus using high-intensity focused ultrasound, a control method thereof, and a skin treatment method using the same, and more particularly to a skin treatment apparatus using radio frequency (RF) energy and ultrasound energy, a control method thereof, and a skin treatment method using the same.

BACKGROUND ART

High-intensity focused ultrasound used for tissue treatment has generally been used in treating cancer cells, but has also been applied to skin with recent technology developed for tissue regeneration.

In a conventional skin treatment apparatus using the high-intensity focused ultrasound, a transducer is actuated as exposed to a liquid environment so that the ultrasound can be increased in propagation efficiency when propagating through a medium. Such a conventional treatment apparatus using the high-intensity focused ultrasound has been disclosed in Korean Patent No. 1246557.

However, the conventional treatment apparatus using the high-intensity focused ultrasound transmits only ultrasound energy to the tissue, thereby having problems of increasing treatment time and increasing tissue recovery time. Further, the transducer needs to be waterproofed to change its position in the liquid environment, thereby having problems of a complicated structure and more causes of failure.

DISCLOSURE

Technical Problem

The disclosure is conceived to solve the foregoing problems, and an aspect of the disclosure is to provide a skin treatment apparatus using high-intensity focused ultrasound to shorten a treatment time and increase a recovery effect, a control method thereof, and a skin treatment method using the same.

Further, the disclosure is to provide a skin treatment apparatus, which has a simple structure, is improved in stability and is convenient to detachably mount a cartridge, and a control method thereof.

Technical Solution

The disclosure is conceived to solve the foregoing problems, and an aspect of the disclosure is to provide a skin treatment apparatus using high-intensity focused ultrasound to shorten a treatment time and increase a recovery effect, a control method thereof, and a skin treatment method using the same.

Further, the disclosure is to provide a skin treatment apparatus, which has a simple structure, is improved in stability and is convenient to detachably mount a cartridge, and a control method thereof.

According to an embodiment of the disclosure, there is provided a skin treatment apparatus using high-intensity focused ultrasound, including: a handpiece; and a cartridge provided at an end portion of the handpiece and facing toward a first side, the cartridge including: a transducer configured to generate ultrasound to be focused in a treatment area through a tip of the cartridge; and at least one electrode provided in the tip and configured to transmit radio frequency (RF) energy to the treatment area.

Meanwhile, the electrode may be configured to heat the treatment area at a first temperature to improve an efficiency of transmitting the ultrasound.

Further, the transducer may be configured to generate the ultrasound to heat the treatment area at a second temperature higher than the first temperature.

Meanwhile, the first temperature may be a temperature at which coagulation does not occur in a treatment area, and the second temperature may be a temperature at which coagulation occurs in the treatment area.

Meanwhile, the skin treatment apparatus may further include a controller configured to control energy to be transferred to the transducer and the electrode, wherein the controller controls the electrode to heat the tissue at least before the transducer generates the ultrasound.

Further, the electrode may be adjacent to an ultrasound passing area in the tip.

Furthermore, the electrode may include a plurality of electrodes, and include a bipolar electrode.

Meanwhile, the transducer may be configured to be adjusted in position inside the cartridge.

In addition, there is provided a control method of a skin treatment apparatus using high-intensity focused ultrasound, the control method including: transmitting RF energy to at least one electrode provided in a tip of a cartridge of a handpiece; and transmitting energy to a transducer provided in the cartridge to generate ultrasound.

Meanwhile, the control method may further include identifying whether a temperature of a treatment area reaches a first temperature based on a value detected by a sensor after the transmitting the RF energy.

Further, the transmitting the energy to the transducer may include transmitting energy to the treatment area so that the temperature of the treatment area can rise to a second temperature higher than the first temperature.

Here, the first temperature may include a temperature at which coagulation does not occur in the treatment area, and the second temperature may include a temperature at which coagulation occurs in the treatment area.

Meanwhile, the transmitting the RF energy to the electrode may include using a plurality of electrodes disposed around and adjacent to an ultrasound passing area in which the ultrasound generated by the transducer passes through the cartridge.

Meanwhile, the RF energy to the electrode may be performed by transmitting bipolar RF energy.

Meanwhile, the transmitting the energy to the transducer is performed while adjusting a position of the transducer inside the cartridge.

In addition, there is provided a skin treatment method using high-intensity focused ultrasound, including: transmitting radio frequency (RF) energy to an area including a treatment area; and remodeling tissue by transmitting high-intensity focused ultrasound energy to the treatment area.

Meanwhile, the transmitting the RF energy may include heating the treatment area at a first temperature to improve an efficiency of transmitting the ultrasound to the treatment area.

Further, the remodeling the tissue may include remodeling the tissue by heating the treatment area at a second temperature higher than the first temperature.

Here, the first temperature may include a temperature at which coagulation does not occur in the treatment area, and the second temperature may include a temperature at which coagulation occurs in the treatment area.

Meanwhile, the transmitting the RF energy to the area including the treatment area may be performed by transmitting bipolar RF energy.

Further, the remodeling the tissue may include adjusting a focused position of the ultrasound energy.

Furthermore, the transmitting the RF energy may be terminated when the remodeling the tissue performed by adjusting the focused position of the ultrasound energy is terminated.

In addition, there is provided a skin treatment apparatus using high-intensity focused ultrasound, including: a cartridge mounting unit provided at a first side of a handpiece; and a cartridge detachably mounted to a first side of the cartridge mounting unit, wherein a position of an ultrasound transducer is adjusted inside the cartridge by moving a magnet in the cartridge mounting unit.

Here, the cartridge mounting unit may include: a mounting-unit housing including a first side connected to the handpiece, and a second side to which the cartridge is detachably mounted; a first shaft extended inside the mounting-unit housing; and a guide unit movable along the first shaft inside the mounting-unit housing, and including a first magnet.

Further, the cartridge may include: a cartridge housing in which a hermetic space is defined; a second shaft extended inside the cartridge housing; and a transducer holder movable along the second shaft inside the cartridge housing, and including a second magnet, and the transducer may be fastened to a first side of the transducer holder.

Meanwhile, the first shaft and the second shaft may be parallel to each other when the cartridge is mounted to the cartridge mounting unit.

Further, the first magnet may be provided at an end portion of the guide unit facing toward the cartridge, and the second magnet may be provided at an end portion of the transducer holder facing toward the cartridge mounting unit.

Meanwhile, the first magnet and the second magnet may be provided to have different polarities in directions opposite to each other.

Meanwhile, the skin treatment apparatus may further include a sensor configured to detect a position of at least one of the transducer holder and the guide unit inside the cartridge.

Furthermore, the sensor may be provided inside the mounting-unit housing.

Meanwhile, the handpiece may further include: an actuation rod including a first side inserted in the cartridge mounting unit and connected to the guide unit; an actuator configured to provide actuating power to the actuation rod; and a controller configured to control the actuator so that the guide unit can reciprocate a predetermined distance when it is identified that the cartridge is mounted to the cartridge mounting unit.

Meanwhile, the controller may control the actuator based on a value detected by the sensor.

In addition, there is provided a control method of a skin treatment apparatus using high-intensity focused ultrasound, the control method including: identifying whether a cartridge is mounted to a cartridge mounting unit; initializing a position of a transducer inside the cartridge when the cartridge is mounted to the cartridge mounting unit; and adjusting the position of the transducer without contact by adjusting a position of a guide unit provided inside the cartridge mounting unit.

Meanwhile, the transducer may be adjusted in position along the guide unit based on magnetic force.

Meanwhile, the transducer may include a first side fastened by a transducer holder provided inside the cartridge, and the transducer holder and the guide unit may include magnets, respectively.

Meanwhile, a first magnet provided in the guide unit and a second magnet provided in the transducer holder may be disposed to attract each other.

Meanwhile, the initializing the position of the transducer may be performed by making the guide unit reciprocate a predetermined distance.

Further, the adjusting the position of the transducer may include feedback control based on the detected position of the transducer.

Meanwhile, the adjusting the position of the transducer may be performed with the cartridge sealed.

Further, the control method may further include controlling the transducer to receive energy so that the transducer can generate the ultrasound after the adjusting the position of the transducer.

Meanwhile, the control method may further include adjusting a focused position of the transducer based on a control input.

Meanwhile, the identifying whether the cartridge is mounted may include identifying based on a connection signal of an electric circuit, received when the cartridge is mounted.

Advantageous Effects

In present disclosure, the skin treatment apparatus using the focused ultrasound, the control method thereof, and the skin treatment method using the same can reduce the treatment time because a large area can be heated prior to tissue heating and remodeled to heat a target point. It can also enhance the recovery effect by activating cellular activity.

In addition, the skin treatment apparatus and the control method using the high-intensity focused ultrasound has the effect of securing the operational stability by being able to move the transducer while independently maintaining the environment in the cartridge with a simple configuration. Furthermore, since the transducer can be automatically coupled and moved when the cartridge is mounted, there is an effect of improving convenience.

DESCRIPTION OF DRAWINGS

The above and/or other aspects will become apparent and more readily appreciated from the following description of embodiments, taken in conjunction with the accompanying drawings, in which.

MODE FOR INVENTION

Figure 1:
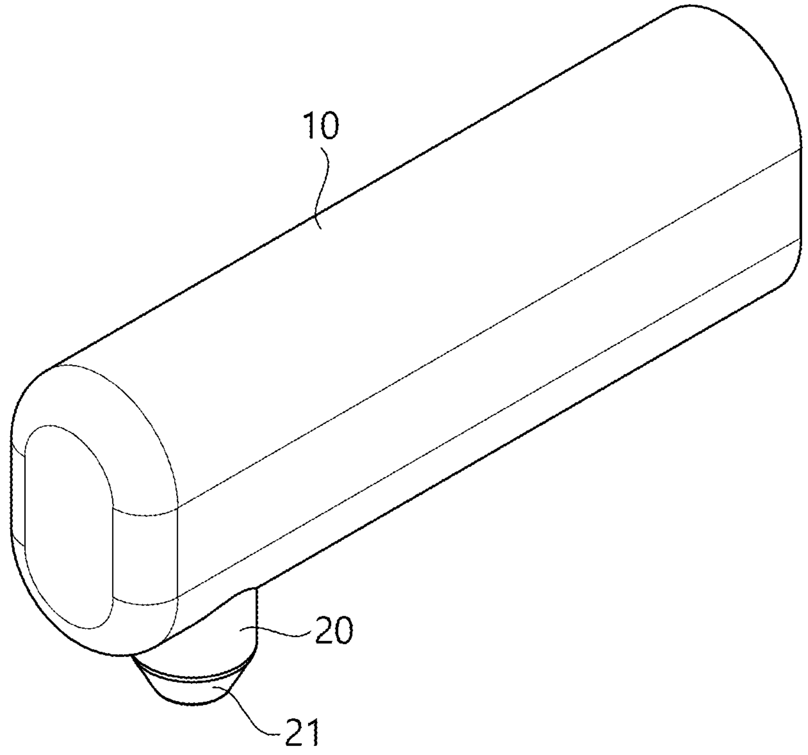
FIG. 1 is a perspective view showing a handpiece of a skin treatment apparatus using high-intensity focused ultrasound according to an embodiment of the disclosure.

Below, a skin treatment apparatus using high-intensity focused ultrasound, a control method thereof, and a skin treatment method using the same according to an embodiment of the disclosure will be described in detail with reference to accompanying drawings. Elements described in embodiments set forth herein may be called other names in the art. However, if the elements are similar or identical in terms of their functions, they may be regarded as equivalents even in alternative embodiments. Further, symbols assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

Treatment according to the disclosure will be described on the premise that it locally heats skin tissue to have effects on improving wrinkles, tone and textural changes, scars and acne scarring, sagging mucosa, overall rejuvenation, hyperhidrosis, laxity, lifting, tightening, fat reduction, etc.

Below, a skin treatment apparatus using high-intensity focused ultrasound according to a first embodiment of the disclosure will be described with reference to FIGS. 1 to 9.

FIG. 1 is a perspective view showing a handpiece 10 of a skin treatment apparatus using high-intensity focused ultrasound according to an embodiment of the disclosure.

As shown therein, the skin treatment apparatus using the high-intensity focused ultrasound according to the first embodiment of the disclosure may include a handpiece 10, and a cartridge 20 provided at an end of the handpiece 10. The handpiece 10 is gripped by a user to locate a tip 21 of the cartridge 20 at a desired position and perform the treatment. Although it is not shown, the handpiece 10 may include a cable at one side thereof to be connected to a main body of the skin treatment apparatus.

Figure 2:
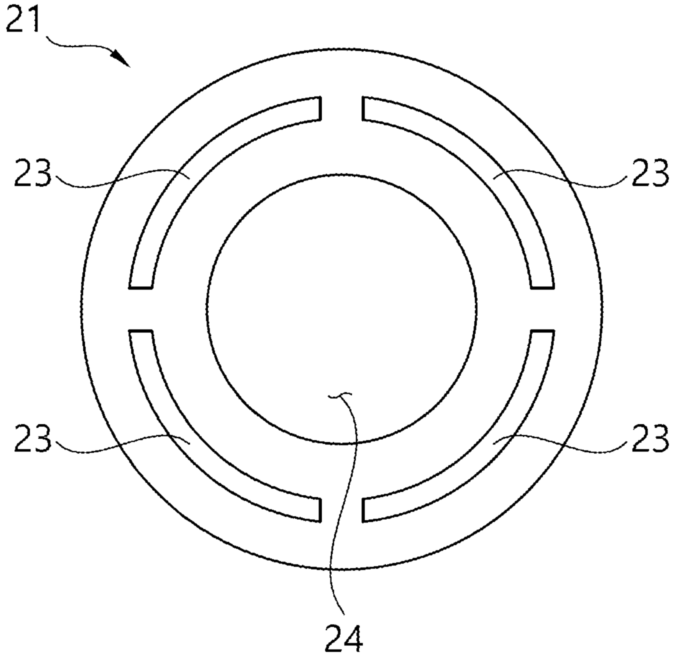
FIG. 2 is a bottom view showing a tip of a cartridge according to a first embodiment.

FIG. 2 is a bottom view showing the tip 21 of the cartridge 20 according to the first embodiment.

Referring to FIG. 2, the tip 21 of the cartridge 20 is structured to become in close contact with skin. The tip 21 may be formed with an ultrasound passing area at a center portion thereof, and include a plurality of electrodes 23 around the ultrasound passing area. An ultrasound transducer 22 provided in the cartridge 20 is configured to transmit ultrasound energy to treatment area Vt through the ultrasound passing area, and the electrodes 23 is configured to transmit radio frequency (RF) energy to the treatment area Vt to be heated. The electrodes 23 may be provided in the form of surrounding the ultrasound passing area, along arc-shaped paths.

Figure 3:
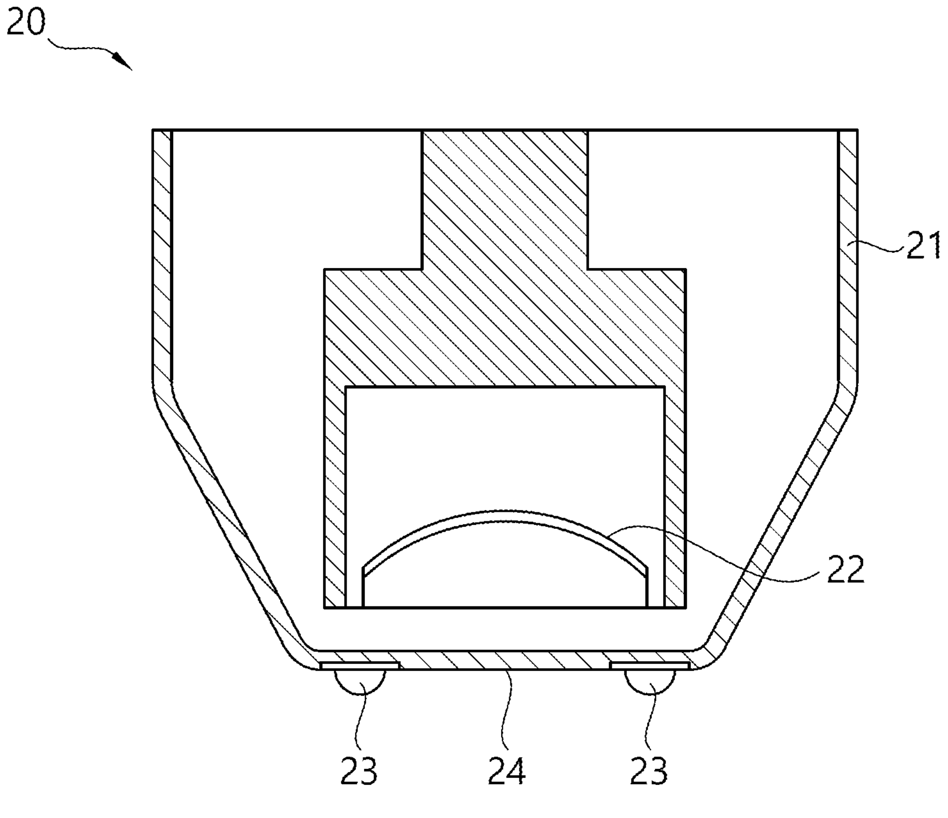
FIG. 3 is a cross-sectional view of the cartridge according to the first embodiment.

FIG. 3 is a cross-sectional view of the cartridge 20 according to the first embodiment.

Referring to FIG. 3, the ultrasound transducer 22 may be provided inside the cartridge 20 and configured to generate ultrasound. Further, the cartridge 20 may include the plurality of electrodes 23 at an end thereof. The cartridge 20 may be sealed up as internally filled with a liquid medium for transmitting the ultrasound.

Figure 4:
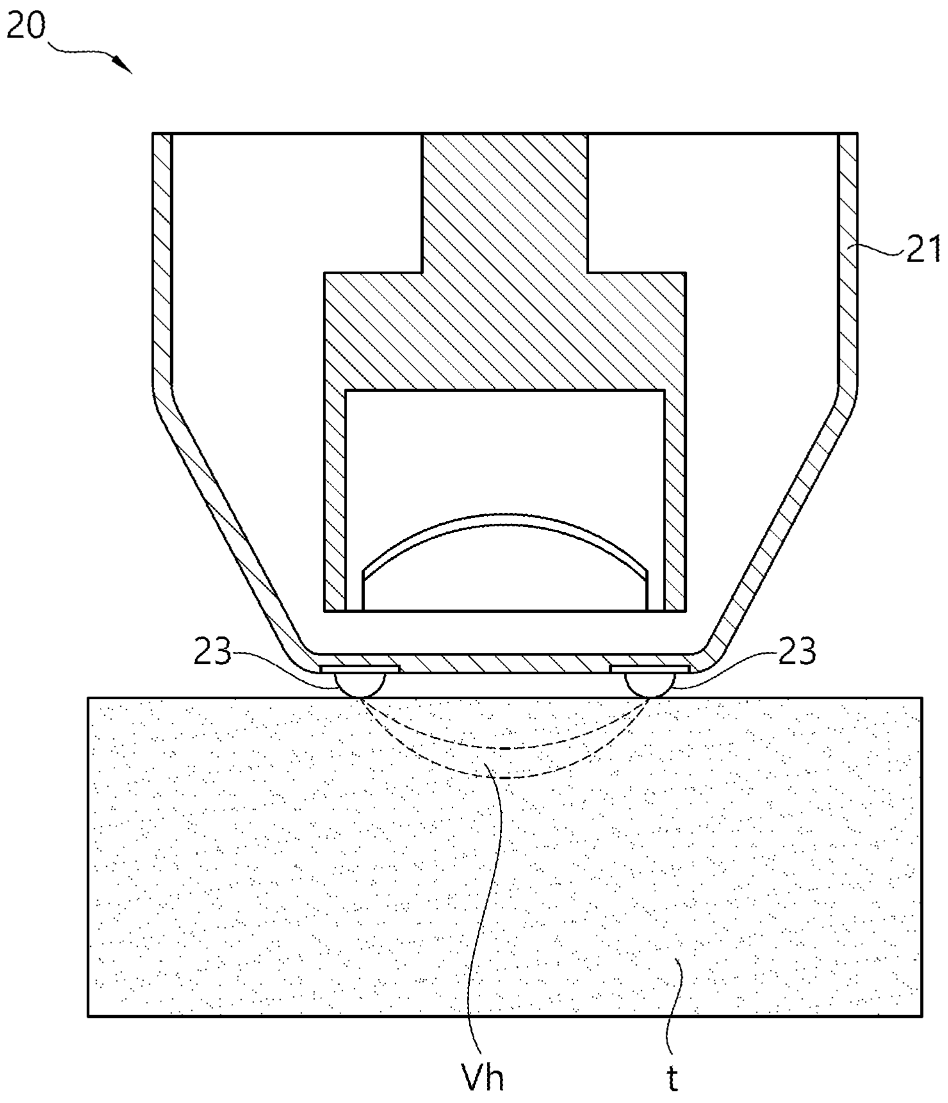
FIG. 4 illustrates concept of transmitting radio frequency (RF) energy through electrodes according to the first embodiment.

FIG. 4 illustrates concept of transmitting the RF energy through the electrodes 23 according to the first embodiment.

Referring to FIG. 4, the electrodes 23 transmit the RF energy while the tip 21 of the cartridge 20 according to this embodiment is in close contact with skin. The RF energy may for example include bipolar RF energy. In this case, a transmission path for the RF energy is formed by one pair of coupled electrodes 23 when the bipolar RF energy is applied, and tissue t is heated along the transmission path for the RF energy to thereby form a heating area Vh throughout a wide area.

In this case, the wide area including the treatment area Vt is heated by the electrodes 23 disposed around the ultrasound passing area 24. The RF energy transmitted by the electrodes 23 may increase the temperature of the treatment area Vt up to a first temperature. The first temperature refers to a temperature at which coagulation does not occur in the treatment area Vt, and may for example be about 45° C. When the tissue t receives the RF energy through the wide area and is heated at the first temperature, cells in the tissue t including the treatment area Vt are improved in activity without damaging the tissue t. The improvement in the activity of the cells in the tissue t helps to generate and recover the skin and exhibit improvement in thin wrinkles and skin tone. In this case, the power and frequency of the RF energy to be transmitted may vary depending on the depth of the tissue t, the distance between the electrodes 23, etc., and therefore description about detailed numerical values thereof will be omitted.

Figure 5:
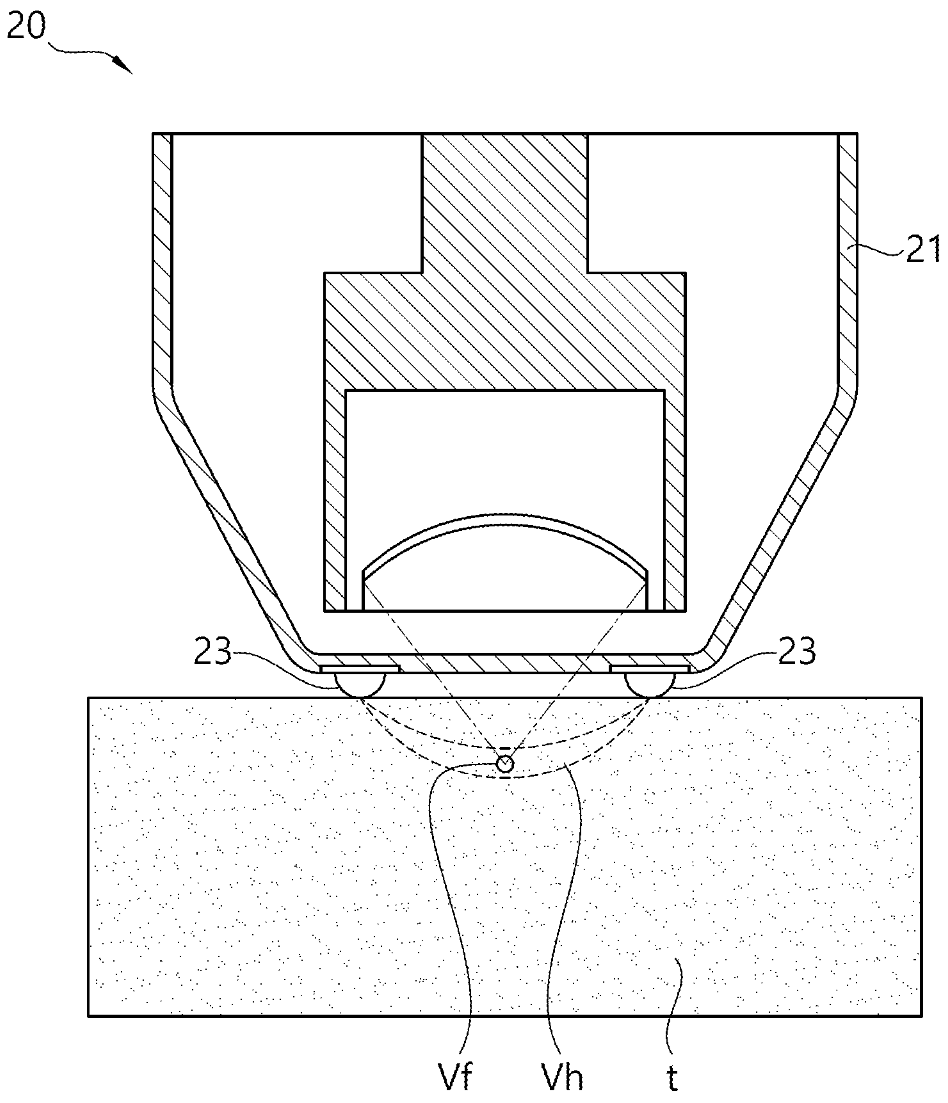
FIG. 5 illustrates concept of transmitting ultrasound energy according to the first embodiment.

FIG. 5 illustrates concept of transmitting ultrasound energy according to the first embodiment.

Referring to FIG. 5, the ultrasound energy generated by the ultrasound transducer 22 passes through the tip 21 of the cartridge 20 and is focused on an ultrasound focal zone Vf in the tissue t. In the ultrasound focal zone Vf, the energy is focused to locally heat the tissue t up to the second temperature. The second temperature refers to a temperature at which the tissue t can be remodeled, and may for example be about 70° C. at which coagulation may occur.

Referring back to FIGS. 4 and 5, according to the first embodiment of the disclosure, the RF energy is first transmitted by the electrode 23 to heat a first area, i.e., a wide area including the treatment area Vt, at the first temperature, and then the ultrasound is focused by the transducer 22 to heat a second area, in which the focal zone Vf is treated, at the second temperature, thereby remodeling the tissue t. When the RF energy is transmitted to heat the first area, the cells are improved in activity without directly remodeling the tissue t. Further, the RF energy is used to preheat the tissue t, and an initial temperature becomes high when the ultrasound is transmitted, thereby making it easy to heat the tissue t at the second temperature even though ultrasound of low energy is used. Therefore, an efficiency of transmitting the high-intensity focused ultrasound is improved.

Figure 6:
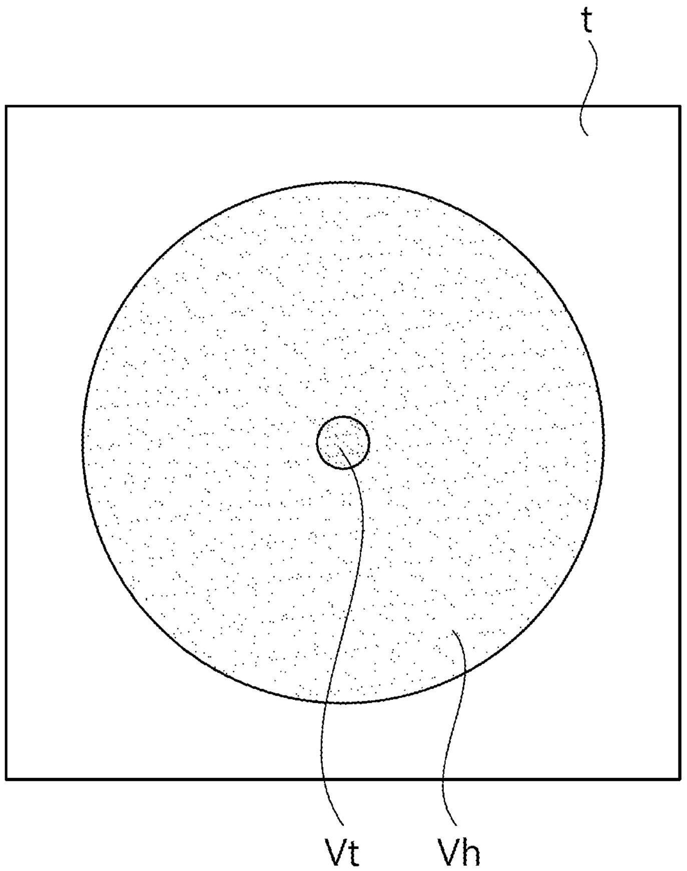
FIG. 6 is a plan view illustrating concept of a heating area and a treatment area in tissue according to the first embodiment.

FIG. 6 is a plan view illustrating concept of the heating area Vh and the treatment area Vt in tissue according to the first embodiment.

FIG. 6 illustrates a cross-section of the tissue T at a depth up to which the ultrasound is focused. The RF energy transmitted to the tissue t through the electrodes 23 heats the wide first area, and thus the temperature of the first area rises up to the first temperature. Meanwhile, the ultrasound energy transmitted by the transducer 22 is focused on the second area, and thus the temperature of the second area rises up to the second temperature. As described above, the second temperature is about 70° C., at which the coagulation of the tissue t occurs. To remodel the wide area through the skin treatment apparatus according to the disclosure, a user controls the position of the handpiece 10, i.e., the position at which the tip 21 is in contact with the skin, to transmit the RF energy and the ultrasound energy. In this case, a process of applying the RF energy and the ultrasound energy may be performed while repetitively changing the position.

Meanwhile, although it is not shown, the control of the RF energy may be performed based on a temperature estimated in the tissue t. For example, the tissue t may be varied in impedance depending on change in the temperature, and it is thus possible to estimate the current temperature deep inside the tissue t based on the impedance of the tissue t or the variation in the impedance. Further, the temperature deep inside the tissue t may be experimentally estimated by measuring the temperature of the skin's surface and considering a temperature gradient in the tissue t.

When it is identified by the temperature deep inside the tissue t, estimated by the controller through various methods, rises up to the first temperature, the controller stops the transmission of the RF energy.

Meanwhile, when the tip 21 of the handpiece 10 is moved to remodel other areas in addition to the second area within the first area of FIG. 6, the tissue t may still have a temperature close to the first temperature. Even in this case, the controller may estimate the temperature of the tissue t by the foregoing method, and stop the transmission of the RF energy when it is identified that the temperature of the tissue t rises up to the first temperature by the transmission of the RF energy. In this case, time taken until the temperature of the tissue t rises up to the first temperature may be shorter than time taken in initially heating the tissue t.

Meanwhile, it is necessary to check sound velocity and impedance versus temperature in order to identify the transmission efficiency of the ultrasound.

Figure 7:
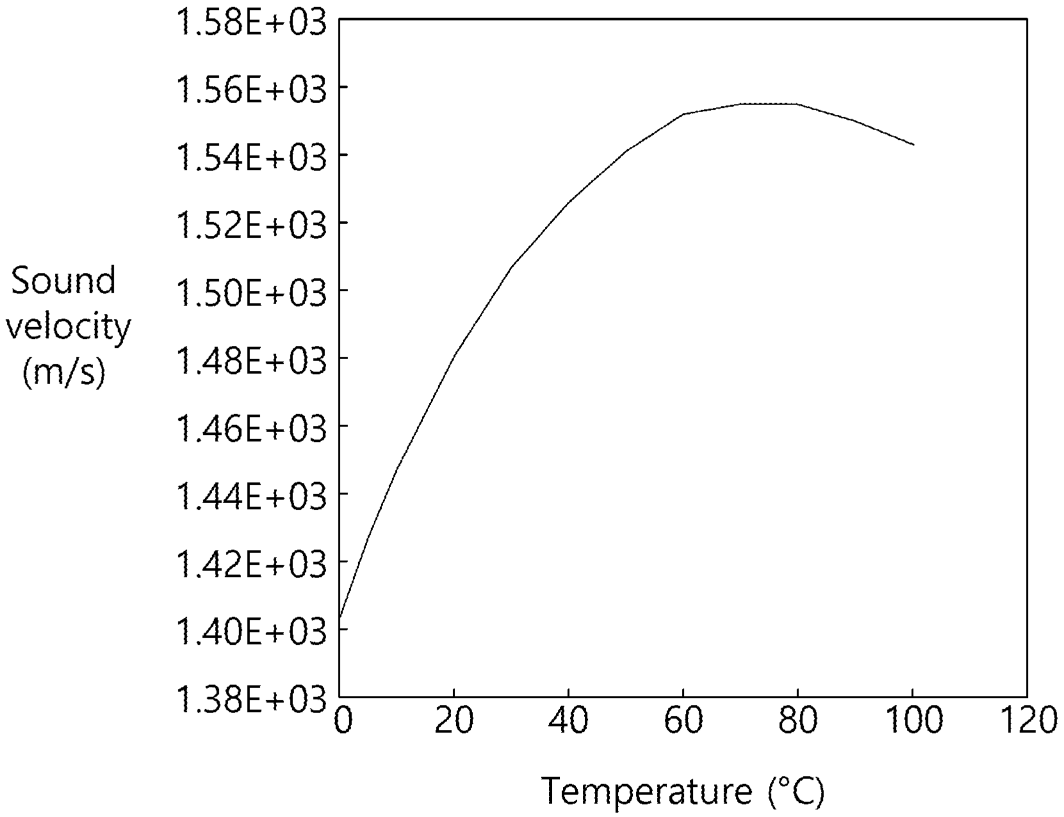
FIG. 7 is a graph of sound velocity versus water temperature.

FIG. 7 is a graph of sound velocity versus water temperature.

Referring to FIG. 7, sound velocity versus water temperature goes up sharply from 0° C. to 60° C. and gently from 60° C. to 80° C., and goes down from 80° C. to 100° C.

Figure 8:
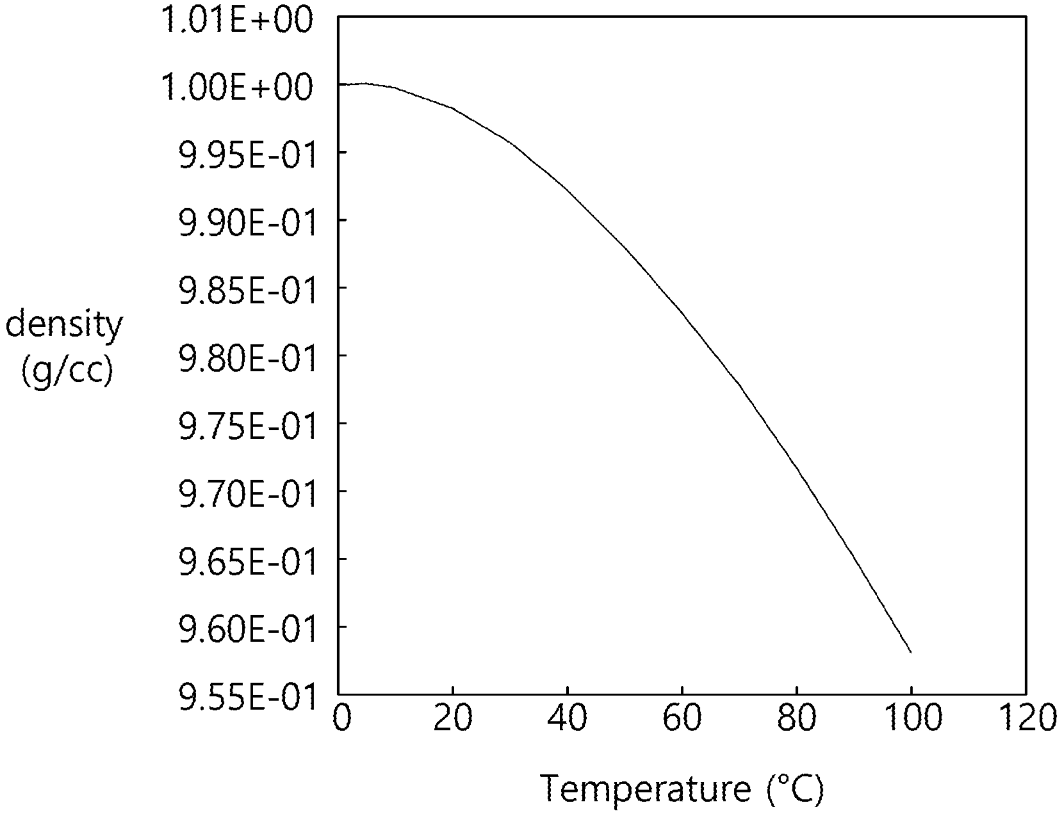
FIG. 8 is graph of water density versus temperature.

FIG. 8 is graph of water density versus temperature;

Referring to FIG. 8, a decrease rate of the water density gradually increases as the water temperature rises from 0 to 100° C.

Figure 9:
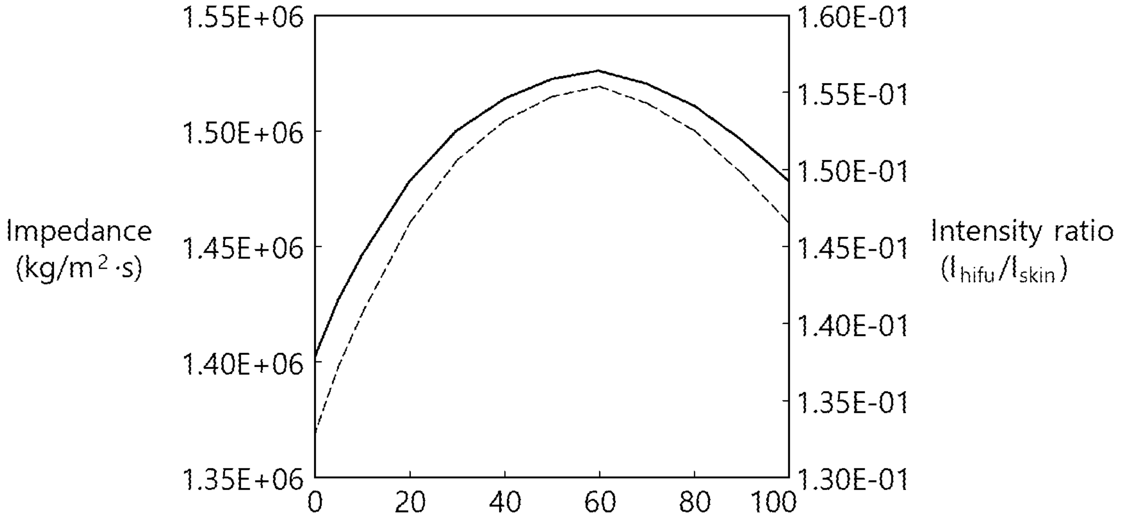
FIG. 9 is a graph of intensity ratio of ultrasound versus temperature.

FIG. 9 is a graph of intensity ratio of ultrasound versus temperature.

Referring to FIG. 9, it is possible to find out water impedance and an intensity ratio ($I_{HIFU}/I_{skin}$) versus the temperature, and the intensity of the ultrasound increases when water impedance approaches a geometric mean $\sqrt{xy}$ between the impedances of the Hifu transducer 22 and the skin impedance.

In other words, the ultrasound is transmitted with the maximum intensity at $Z_{water}=\sqrt{Z_{Transducer}Z_{skin}}$. Because the general transducer 22 has an impedance of 3.5×107 (kg/m$^2$s) and the skin has an impedance of 1.6×106 (kg/m$^2$s), the intensity of the ultrasound increases when the water impedance increases as the water temperature increases. This tendency is maintained until water is heated up to the temperature of 60° C., and the transmission efficiency of the ultrasound is maximized when the water temperature is 60° C.

Therefore, the RF energy is used in appropriately heating the tissue t before applying the ultrasound to the tissue t, thereby improving the transmission efficiency of the ultrasound. However, when the tissue t is heated up to 60° C. so as to maximize the efficiency of the ultrasound as described above, the tissue t is damaged a lot and it is thus difficult to achieve the goal of improving cell activity. Therefore, the first temperature may be set as a temperature at which protein is appropriately denaturalized without the damage of the tissue t. The first temperature may approximate to 45° C., and the tissue t heated to have the first temperature is increased in the transmission efficiency of the ultrasound and improved in the activity of the cells, thereby helping to recover the tissue t.

Below, a skin treatment apparatus using high-intensity focused ultrasound according to a second embodiment of the disclosure will be described in detail with reference to FIGS. 10 to 14. This embodiment may also include the same elements as described in the foregoing embodiment, and repetitive descriptions of such elements will be avoided.

Figure 10:
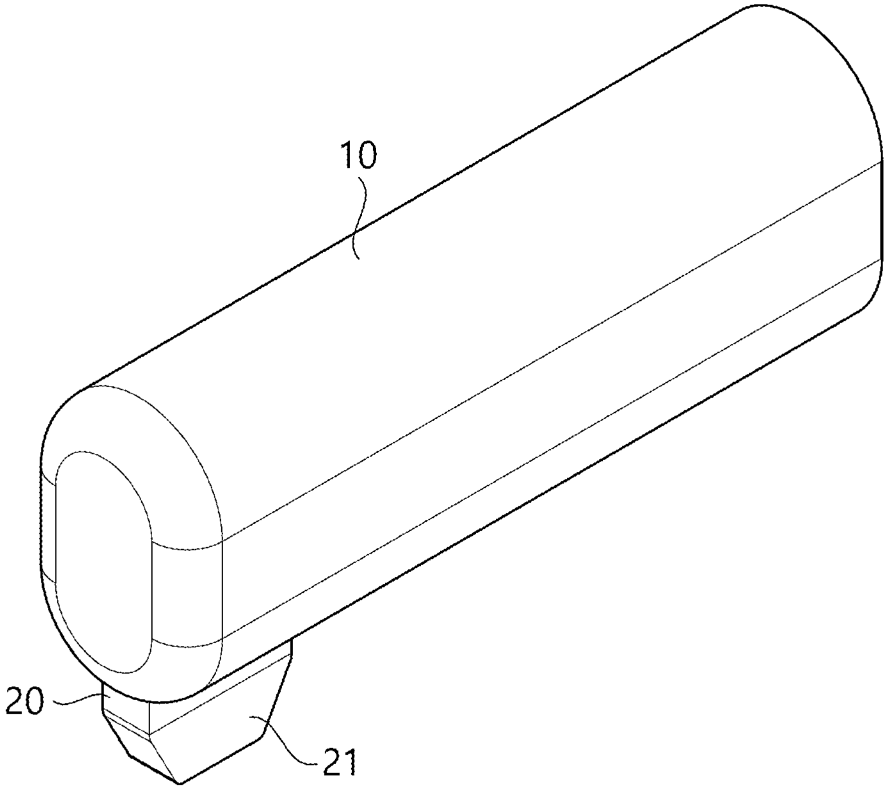
FIG. 10 is a perspective view of a skin treatment apparatus using high-intensity focused ultrasound according to a second embodiment of the disclosure.
Figure 11:
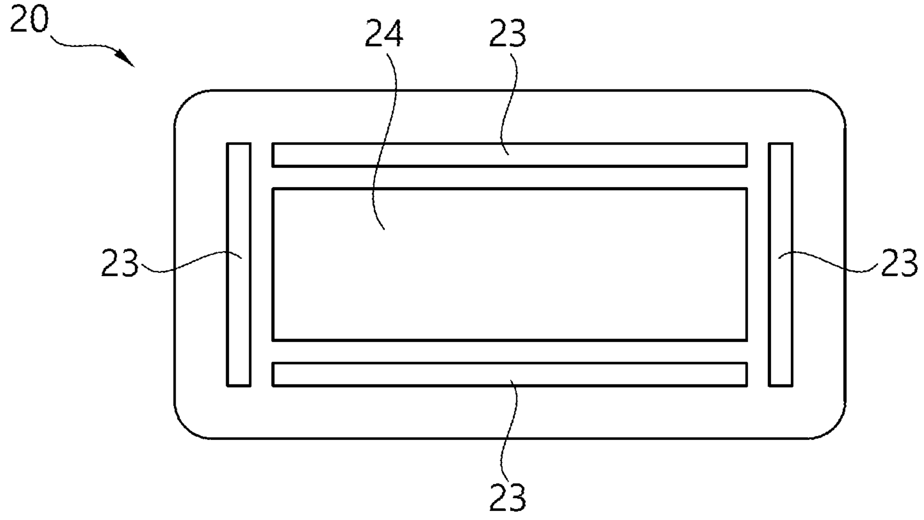
FIG. 11 is a bottom view showing an end of a tip according to the second embodiment.
Figure 12:
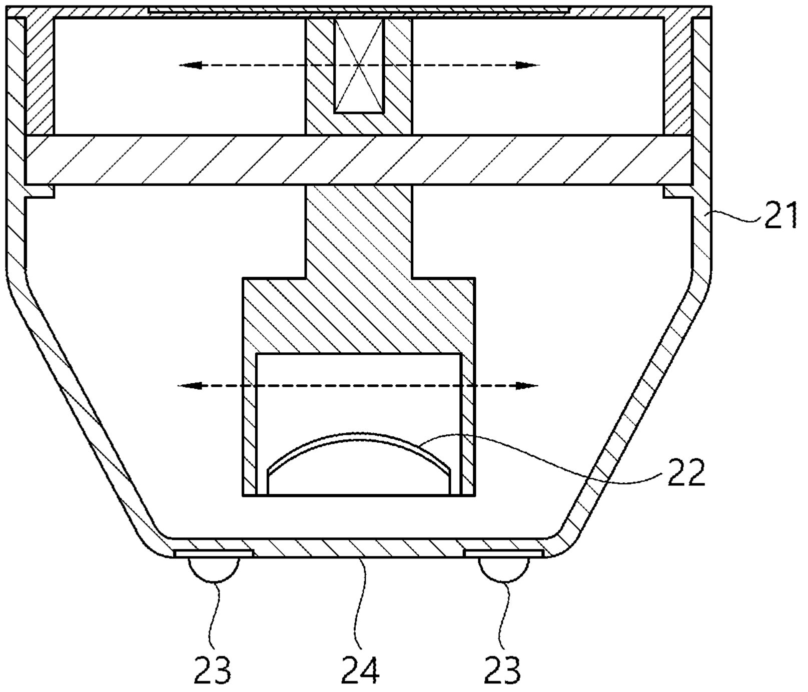
FIG. 12 is a cross-sectional view of the tip according to the second embodiment.

FIG. 10 is a perspective view of the skin treatment apparatus using high-intensity focused ultrasound according to the second embodiment of the disclosure, FIG. 11 is a bottom view showing the end of the tip 21 according to the second embodiment, and FIG. 12 is a cross-sectional view of the tip 21 according to the second embodiment.

Referring to FIGS. 10 to 12, the skin treatment apparatus using the high-intensity focused ultrasound according to the second embodiment of the disclosure may include the transducer 22 that can reciprocate in one direction within the cartridge 20. In other words, the second area may be formed at a plurality of points by moving the transducer 22 in the state that the tip 21 of the cartridge 20 is maintained as being is in close contact with the skin.

In this case, the electrodes 23 may be disposed to surround the ultrasound passing area 24 varied depending on the movement of the transducer 22.

The cartridge 20 may include an actuator to adjust the position of the transducer 22 inside the cartridge 20. The actuator is provided to make the transducer 22 reciprocate in one direction.

Figure 13:
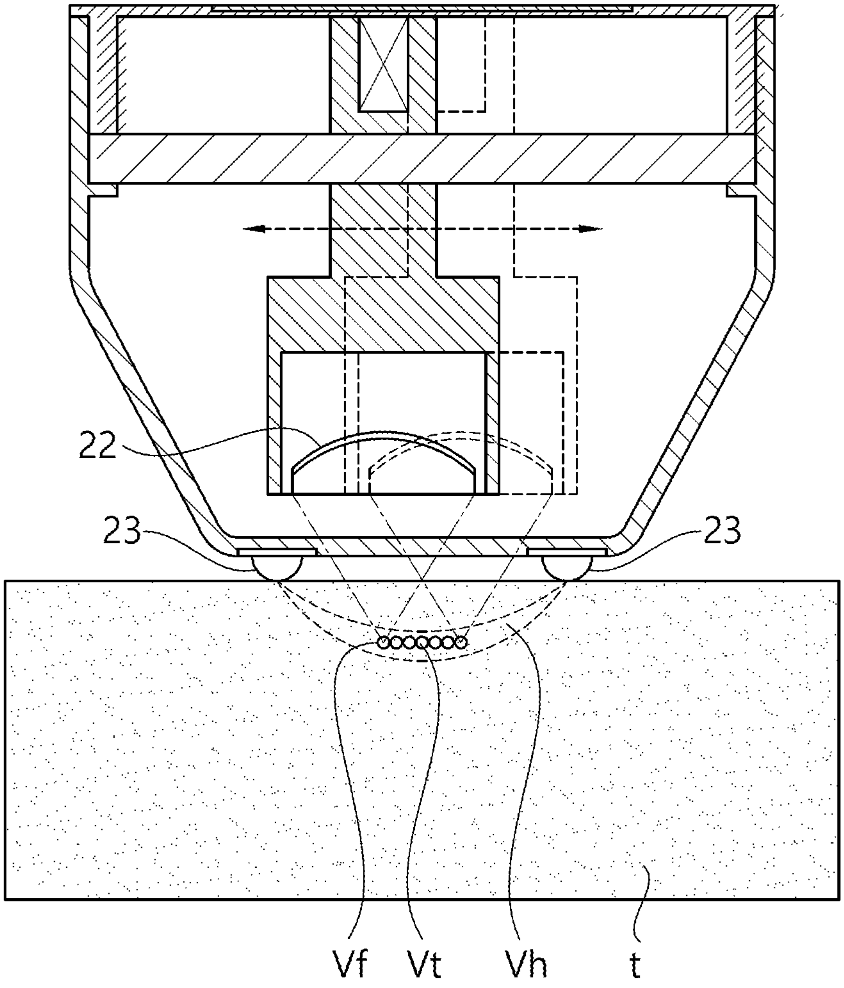
FIG. 13 illustrates operating states according to the second embodiment.

FIG. 13 illustrates operating states according to the second embodiment.

Referring to FIG. 13, according to the second embodiment, the ultrasound energy is transferred while moving the transducer 22 after the RF energy is transmitted through the electrodes 23. The controller performs repetitive operations of applying the ultrasound energy after the transducer 22 moves a predetermined distance based on a preset algorithm, and applying the ultrasound energy after the transducer 22 moves a predetermined distance again. Then, when the transducer 22 is moved up to the end point, the treatment at a current location may be completed.

Figure 14:
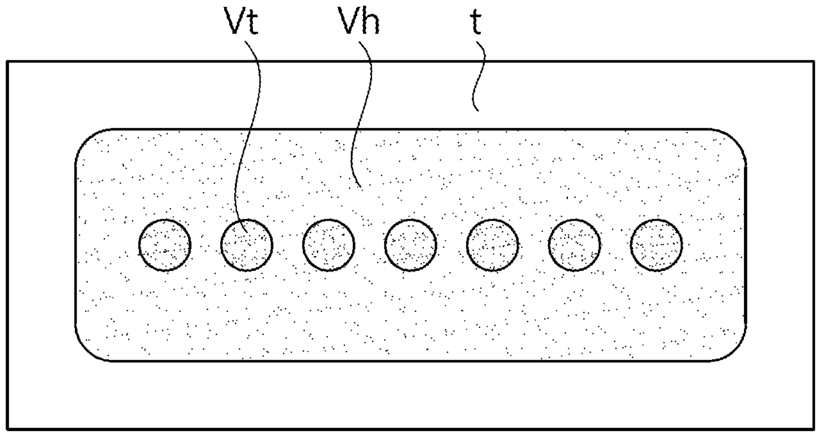
FIG. 14 is a plan view illustrating concept of a heating area and a treatment area according to the second embodiment.

FIG. 14 is a plan view illustrating concept of the heating area Vh and the treatment area Vt according to the second embodiment. Referring to FIG. 14, according to this embodiment, the area to which the RF energy is transmitted through the electrodes 23 may be elongated, so that the second area can be formed at a plurality of points as its position is adjusted within the heated first area in a horizontal direction. Like this, when the transducer 22 is movable, the treatment may be automatically carried out throughout the wide area even though a user does not move the handpiece 10 every time, and it is possible to minimize a user's intervention. Further, it is also possible to shorten overall treatment time because there are no needs of repetitively moving the handpiece 10.

Below, a method of controlling a skin treatment apparatus using high-intensity focused ultrasound according to a third embodiment of the disclosure will be described with reference to FIG. 15.

Figure 15:
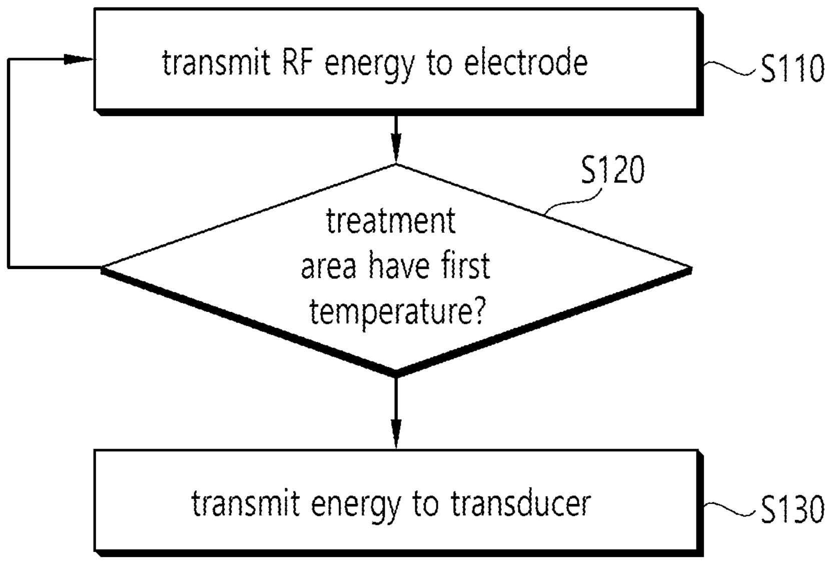
FIG. 15 is a flowchart showing a control method of a skin treatment apparatus using high-intensity focused ultrasound according to a third embodiment of the disclosure.

Referring to FIG. 15, the method of controlling the skin treatment apparatus using high-intensity focused ultrasound according to the third embodiment of the disclosure may include operation S110 of transmitting the RF energy to the electrodes, operation S120 of identifying whether the treatment area is heated up to the first temperature, and operation S130 of transmitting the energy to the transducer.

The operation S110 of transmitting the RF energy to the electrodes refers to operation of transmitting the RF energy to tissue through the electrodes being in contact with the tissue. When the RF energy is transmitted to the tissue, deep heat is generated in the tissue so that temperature can rise in the wide area including the treatment area.

The operation S120 of identifying whether the treatment area is heated up to the first temperature refers to operation of estimating the temperature of the treatment area and identifying whether the estimated temperature is the first temperature. This operation may be performed based on the temperature of a deep part, which is estimated from the temperature of a skin surface measured by a temperature sensor provided in the handpiece. Alternatively, the temperature may be estimated based on the impedance of the tissue, with which the electrodes are in contact, or based on variation in the impedance. The first temperature may be about 45° C., at which cell activity is promoted but excessive denaturation is prevented.

The operation 130 of transmitting the energy to the transducer refers to operation of transmitting energy so that the ultrasound energy can be focused on the treatment area by the transducer. In this operation, the energy transmitted to the transducer passes through the skin and is finally focused in the deep part, thereby heating the tissue. While the ultrasound energy is being focused, the tissue may be heated up to the second temperature at which coagulation occurs. The second temperature may be about 70° C.

Meanwhile, the foregoing control method according to the third embodiment may be performed in the skin treatment apparatus using the high-intensity focused ultrasound, described with reference to FIGS. 1 to 6.

Below, a method of controlling a skin treatment apparatus using high-intensity focused ultrasound according to a fourth embodiment will be describe with reference to FIG. 16.

Figure 16:
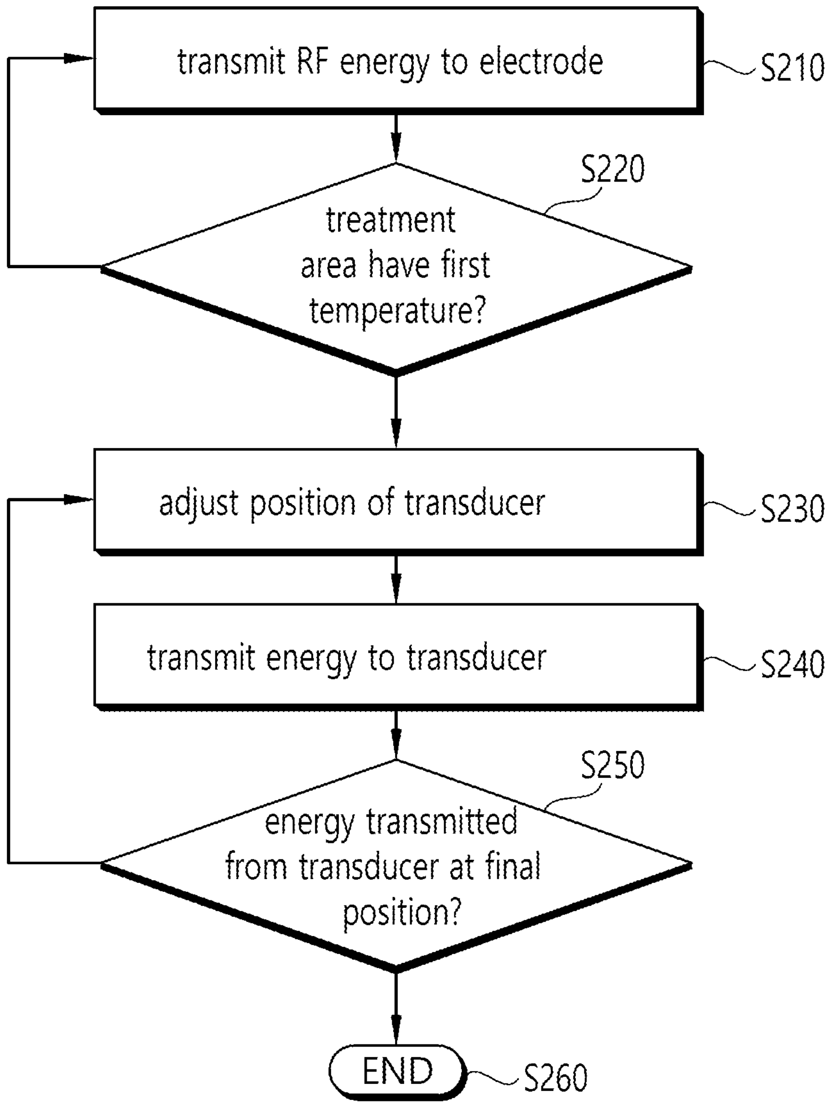
FIG. 16 is a flowchart showing a control method of a skin treatment apparatus using high-intensity focused ultrasound according to a fourth embodiment of the disclosure.

FIG. 16 is a flowchart showing a control method of the skin treatment apparatus using the high-intensity focused ultrasound according to the fourth embodiment of the disclosure.

Referring to FIG. 16, the method of controlling the skin treatment apparatus using the high-intensity focused ultrasound according to the fourth embodiment of the disclosure may include operation S210 of transmitting the RF energy to the electrodes, operation S220 of identifying whether the treatment area is heated up to the first temperature, operation S230 of adjusting the position of the transducer, operation S240 of transmitting the energy to the transducer, and operation S250 of identifying whether the transducer transmits the energy at the final position.

The operation S210 of transmitting the RF energy to the electrodes and the operation S220 of identifying whether the treatment area is heated up to the first temperature may be performed like the foregoing operation S110 of transmitting the RF energy to the electrodes and the foregoing operation S120 of identifying whether the treatment area is heated up to the first temperature.

The operation S230 of adjusting the position of the transducer refers to operation of adjusting the position of the transducer to define the treatment area. This operation may be carried out by adjusting the position of the transducer inside the cartridge.

The operation S240 of transmitting the energy to the transducer refers to operation of transmitting the ultrasound energy from the adjusted position of the transducer to the treatment area to thereby locally generate heat. In this operation, the tissue is heated up to the second temperature, thereby causing the coagulation of the tissue and eventually remodeling the tissue.

Meanwhile, the foregoing operation 210 of transmitting the RF energy to the electrodes may be continuously performed even while the operation S230 of adjusting the position of the transducer and the operation S240 of transmitting the energy to the transducer are being performed.

The operation S250 of identifying whether the transducer transmits the energy at the final position refers to operation of identifying whether the ultrasound transducer that can reciprocate inside the cartridge along one direction transmits the ultrasound energy as positioned at the end point.

When it is identified that the transducer does not transmit the energy yet at the final position in the foregoing operation S250 of identifying whether the transducer transmits the energy at the final position, the operations S230 and 240 of adjusting the position of the transducer and transmitting the energy to the transducer may be repetitively performed.

On the other hand, when it is identified that the transducer transmits the energy at the final position, it is identified that the treatment is finished in the area where the handpiece is currently positioned, thereby terminating the transmission of the energy (S260). In this case, the RF energy transmitted to the electrodes is also terminated, thereby terminating the transmission of all the energy.

Thereafter, this embodiment may be carried out again when a user changes the treatment location and then puts the tip of the handpiece onto the skin.

Meanwhile, the foregoing control method according to the fourth embodiment may be performed in the skin treatment apparatus using the high-intensity focused ultrasound described with reference to FIGS. 10 to 14.

Below, a skin treatment method using high-intensity focused ultrasound according to a fifth embodiment of the disclosure will be described with reference to FIG. 17.

Figure 17:
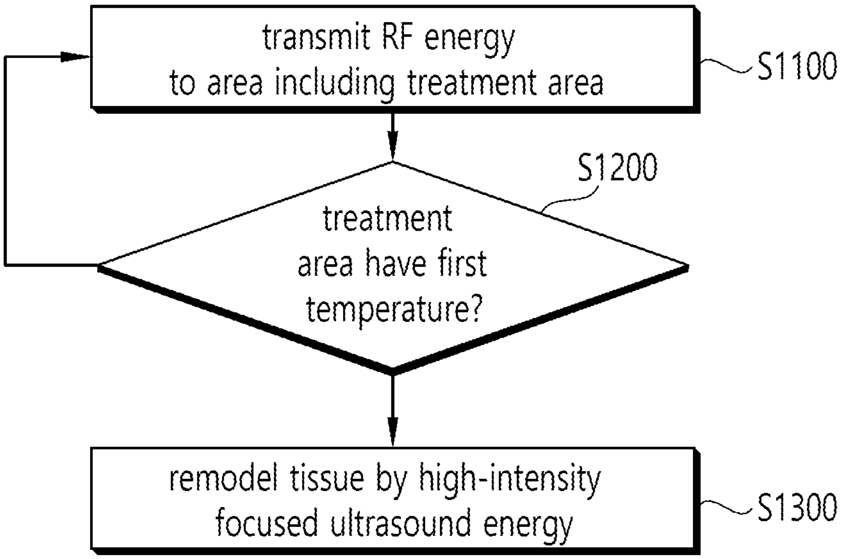
FIG. 17 is a flowchart showing a skin treatment method using high-intensity focused ultrasound according to a fifth embodiment of the disclosure.

FIG. 17 is a flowchart showing a skin treatment method using high-intensity focused ultrasound according to a fifth embodiment of the disclosure.

Referring to FIG. 17, the skin treatment method using the high-intensity focused ultrasound according to the fifth embodiment of the disclosure may include operation S1100 of transmitting the RF energy to an area including a treatment area, operation S1200 of identifying whether the treatment area is heated up to the first temperature, and operation S1300 of transmitting the high-intensity focused ultrasound energy to remodel tissue.

The operation S1100 of transmitting the RF energy to the energy including the treatment area refers to operation of heating a wide area including the treatment area through the electrodes being in contact with the skin.

The operation S1200 of identifying whether the treatment area is heated up to the first temperature refers to operation of heating the treatment area with the RF energy transmitted to the tissue, at about 45° C. where cell activity is improved and thin wrinkles and skin tone are effectively improved. When the treatment area is not heated up to the first temperature, the RF energy is continuously transmitted to the wide area.

The operation S1300 of transmitting the high-intensity focused ultrasound energy to remodel the tissue refers to operation of transmitting the high-intensity focused ultrasound energy so that the treatment area can be heated up to the second temperature, when it is identified that the treatment area is heated up to the first temperature. The second temperature may refer to a temperature at which coagulation occurs in the treatment area. The second temperature may for example be 70° C.

Meanwhile, the fifth embodiment may be carried out based on the skin treatment apparatus using the ultrasound as described above in the first embodiment.

Below, a skin treatment method using high-intensity focused ultrasound according to a sixth embodiment of the disclosure will be described with reference to FIG. 18.

Figure 18:
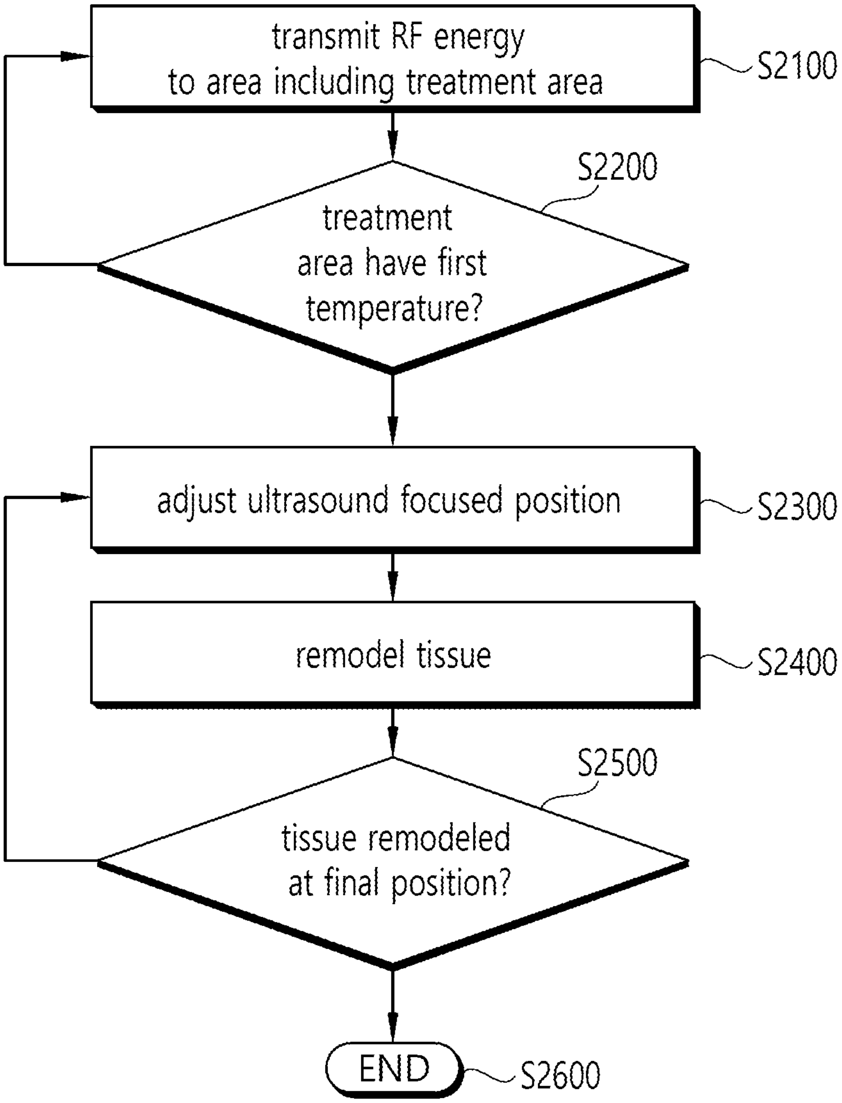
FIG. 18 is a flowchart showing a skin treatment method using high-intensity focused ultrasound according to a sixth embodiment of the disclosure.

FIG. 18 is a flowchart showing the skin treatment method using high-intensity focused ultrasound according to the sixth embodiment of the disclosure.

Referring to FIG. 18, the skin treatment method using high-intensity focused ultrasound according to the sixth embodiment of the disclosure may include operation S2100 of transmitting the RF energy to an area including a treatment area, operation S2200 of identifying whether the treatment area is heated up to the first temperature, operation S2300 of adjusting an ultrasound focused position, operation S2400 of remodeling tissue, and operation S2500 of identifying whether the remodeling of the tissue is performed at a final position.

The operation S2100 of transmitting the RF energy to the area including the treatment area and the operation S2200 of identifying whether the treatment area is heated up to the first temperature may be performed like the foregoing operation S1100 of transmitting the RF energy to the area including the treatment area and the foregoing operation S1200 of identifying whether the treatment area is heated up to the first temperature.

The operation S2300 of adjusting an ultrasound focused position refers to operation of adjusting the focused position by adjusting the position of the ultrasound transducer inside the cartridge provided in the handpiece. In this operation, the position may be adjusted in a direction parallel to the skin surface corresponding to the tissue heated with the transmitted RF energy, and the depth in the tissue corresponding to the focal zone may be adjusted and changed.

The operation S2400 of remodeling the tissue refers to operation of applying the ultrasound energy from the ultrasound transducer to the tissue. The ultrasound energy focused in the tissue locally heats the tissue, thereby forming the treatment area. The ultrasound energy may heat the tissue up to the treatment temperature, i.e., the second temperature. The second temperature may be a temperature at which coagulation enabling the tissue to be remodeled occurs.

The operation S2500 of identifying whether the remodeling of the tissue is performed at the final position refers to operation of identifying whether the remodeling of the tissue is completed as the transducer positioned at the end point transmits the ultrasound energy to the tissue.

When it is identified that the remodeling of the tissue is performed at the final position, the transmission of the energy is terminated (S2600). On the other hand, when it is identified that the remodeling of the tissue is not completed within a moving distance of the transducer, the operations S2300 and S2400 of adjusting the focused position of the ultrasound and remodeling the tissue by moving the transducer to an untreated area may be repetitively performed.

The operation S2100 of transmitting the RF energy to the area including the treatment area may be continuously performed to maintain the first temperature while the operation of adjusting the ultrasound focused position and the operation of remodeling the tissue are carried out.

Meanwhile, the sixth embodiment may be carried out based on the skin treatment apparatus using the ultrasound as described above in the second embodiment.

Below, a skin treatment apparatus 1 using high-intensity focused ultrasound according to a seventh embodiment of the disclosure will be described in detail with reference to FIGS. 19 to 24D.

Figure 19:
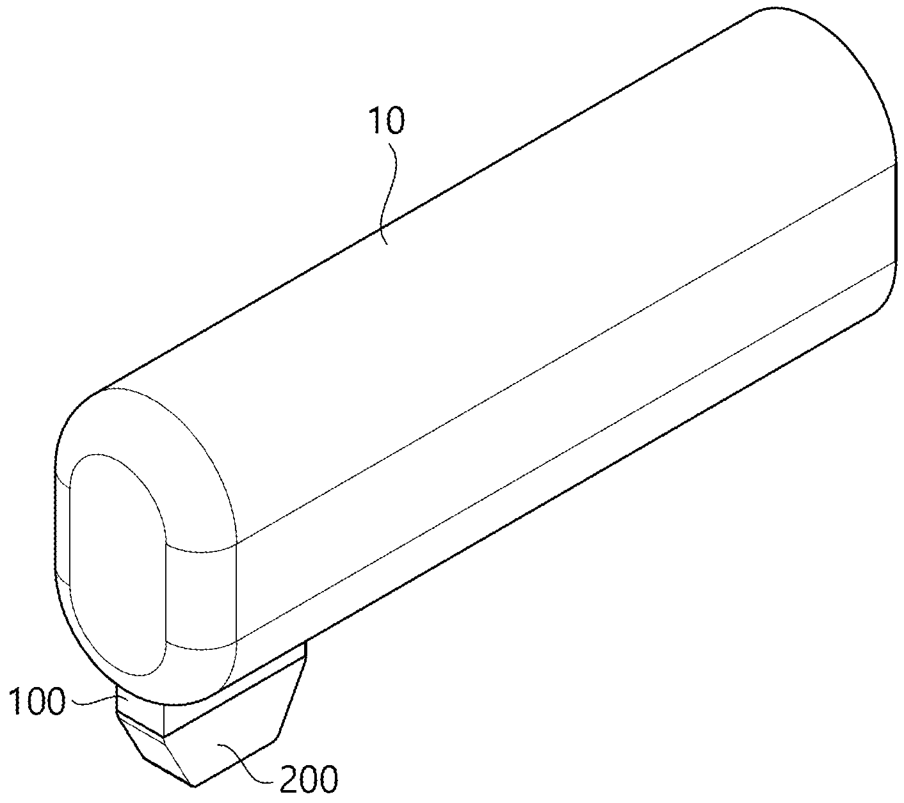
FIG. 19 is a perspective view showing a handpiece of a skin treatment apparatus using high-intensity focused ultrasound according to a seventh embodiment of the disclosure.

FIG. 19 is a perspective view showing a handpiece 10 of the skin treatment apparatus 1 using high-intensity focused ultrasound according to the seventh embodiment of the disclosure.

As shown in FIG. 19, the skin treatment apparatus 1 using the high-intensity focused ultrasound according to the disclosure includes the handpiece 10 to be gripped and used by a user. The handpiece 10 has a first side connected to a main body, and a second side including a cartridge mounting unit 100. The cartridge mounting unit 100 may have a first side to which a cartridge 200 is detachably mounted. A user may move the handpiece 10 to adjust an area, with which the cartridge 200 becomes in close contact, on the skin.

Although it is not shown, there may be separately provided the main body that includes a power supply, a display, and the like elements for monitoring the current state and generating the ultrasound energy. However, widespread elements may be employed as the power supply, the display, and the like elements, and thus detailed descriptions thereof will be omitted.

Meanwhile, the controller may be provided to control the position of a transducer 240 and the energy based on a user's input or a preset algorithm. The controller may be placed in the main body as an integrated controller or may be partially placed inside the handpiece 10 as a sub-controller. The place of the controller may be variously changed and applied.

Figure 20:
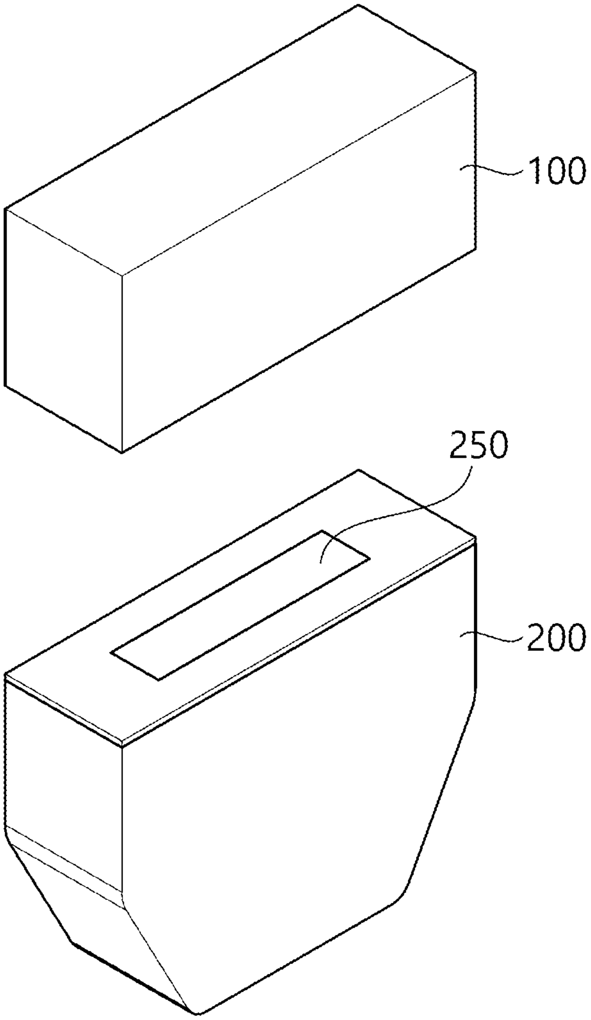
FIG. 20 is an enlarged view of a cartridge and a cartridge mounting unit in the skin treatment apparatus using the high-intensity focused ultrasound according to the seventh embodiment of the disclosure.

FIG. 20 is an enlarged view of the cartridge 200 and the cartridge mounting unit 100 in the skin treatment apparatus 1 using the high-intensity focused ultrasound according to the seventh embodiment of the disclosure.

Referring to FIG. 20, the cartridge 200 in this embodiment may be detachably mounted to the first side of the cartridge mounting unit 100. A user may mount the cartridge 200 to the cartridge mounting unit 100 so as to be ready for use. In this case, the cartridge 200 may be internally filled with a liquid medium m so that the ultrasound can be easily transmitted from a transducer 240. The cartridge 200 is sealed up while accommodating the transducer 240 and the liquid medium m therein, thereby preventing the liquid medium from leakage.

Figure 21:
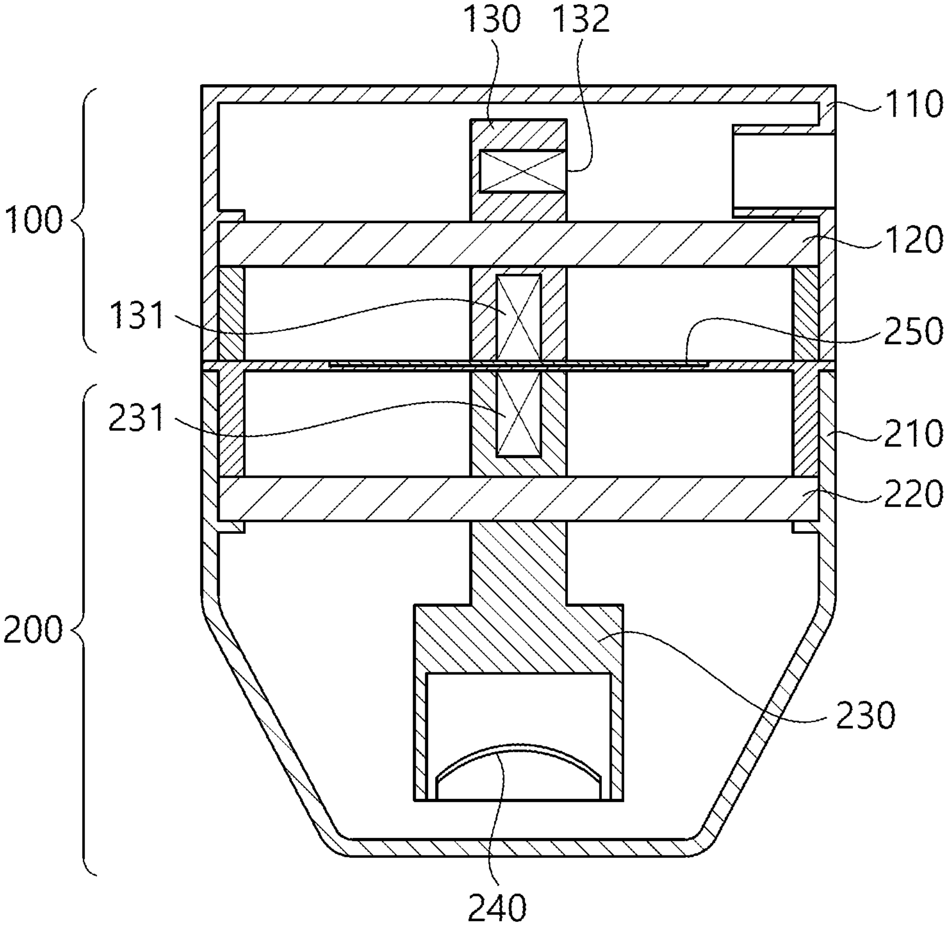
FIG. 21 is a cross-sectional view of the cartridge and the cartridge mounting unit.
Figure 22:
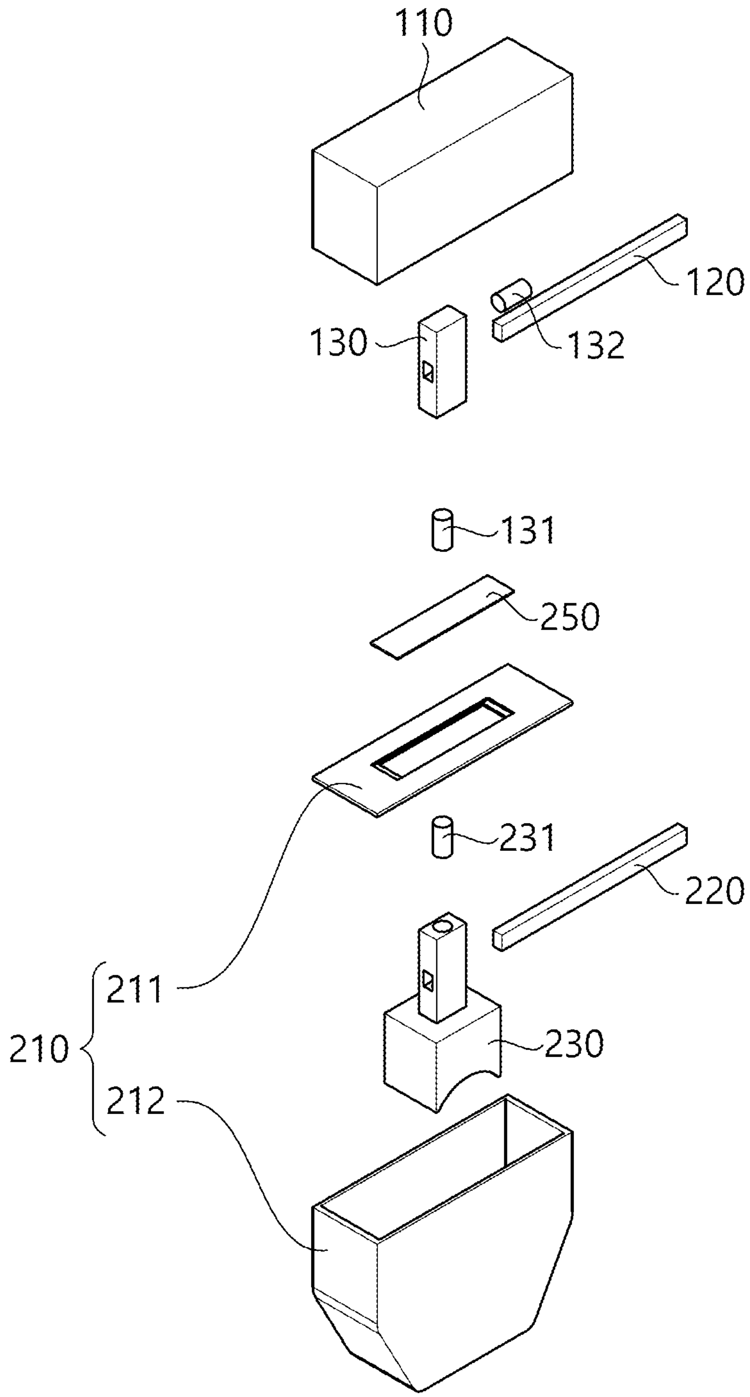
FIG. 22 is an exploded perspective view of the cartridge and the cartridge mounting unit.

FIG. 21 is a cross-sectional view of the cartridge 200 and the cartridge mounting unit 100, and FIG. 22 is an exploded perspective view of the cartridge 200 and the cartridge mounting unit 100.

Referring to FIGS. 21 and 22, the cartridge mounting unit 100 may include a mounting-unit housing 110, a first shaft 120, a guide unit 130, a first magnet 131, and a holding magnet 132.

The mounting-unit housing 110 serves as a base through which the cartridge 200 is mounted to the handpiece 10. The mounting-unit housing 110 is internally formed with a space, and has a first side fastened and installed to the handpiece 10. The mounting-unit housing 110 has the space in which the guide unit 130 (to be described later) can move by an actuation rod 12. The mounting-unit housing 110 may be shaped like a rectangular parallelepiped relatively elongated along the moving direction of the guide unit 130. The mounting-unit housing 110 may have a second side partially cut to accommodate the actuation rod 12 provided of the handpiece 10 therein. For example, the mounting-unit housing 110 may include an insertion hole at a lateral side to insert the actuation rod 12 therein.

The first shaft 120 may be extended along the elongated side and placed inside the mounting-unit housing 110. The first shaft 120 may be provided at a predetermined distance from an end portion of the mounting-unit housing 110, and have opposite ends respectively connected and fastened to the inside of the mounting-unit housing 110. The cross-section of the first shaft 120 may have a rotation-preventing structure to prevent the guide unit 130 moving on the first shaft 120 from rotating. The first shaft 120 may for example have a quadrangular cross-section to prevent the guide unit 130 from rotating. However, although it is not shown, the rotation-preventing structure of the first shaft 120 may be achieved by a projection/groove matching structure to match the guide unit 130.

The guide unit 130 is provided to guide the movement of the holder of the transducer 240 in the cartridge 200 based on magnetic force. The guide unit 130 is provided to reciprocate on the first shaft 120 in one direction. The guide unit 130 may be provided with the holding magnet 132 and a second magnet 231. The guide unit 130 has a hole formed in a horizontal direction, in which the first shaft 120 can be inserted, and is extended up and down having a predetermined length with respect to the hole. Referring to FIG. 21, the holding magnet 132 is provided in an upper portion of the guide unit 130, and has poles oriented toward a lateral side so that magnetic force can be focused in a lateral direction. The first magnet 131 is provided in a lower portion of the guide unit 130, and has poles oriented downward so that magnetic force can be focused in a downward direction.

Eventually, when the position of the guide unit 130 is adjusted inside the cartridge mounting unit 100, the position of the first magnet 131 is adjusted to thereby adjust the position of a transducer holder 230 (to be described later).

The cartridge 200 may include a cartridge housing 210, a second shaft 220, the transducer holder 230, the transducer 240, and the second magnet 231.

The cartridge housing 210 is internally formed with a space, and serves as a base in which the second shaft 220, the transducer holder 230, and the transducer 240 are accommodated. The cartridge housing 210 may have a cross-section shaped like a rectangle elongated in one direction. The cartridge housing 210 may include an upper housing 211 and a lower housing 212. The upper housing 211 may have a hollow in the middle thereof, and include a separation film 250 to cover the hollow. The separation film 250 may be thin and prevent fluid from flowing. The separation film is interposed between the first magnet 131 and the second magnet 231 when the cartridge is mounted to the cartridge mounting unit. Therefore, the distance between the end portion of the first magnet 131 and the end portion of the second magnet 231 is so extremely small that magnetic attraction can be secured.

The cartridge housing 210 may include a contact portion so that its first side can be in close contact with a skin. The contact portion may be flat to minimize the curves of the skin when it is in close contact with the skin, so that uniform transmission of the ultrasound energy can be maintained.

The second shaft 220 may be parallel with the long side in the cartridge housing 210. The second shaft 220 may be disposed at an angle to be parallel with the first shaft 120 when the cartridge 200 is mounted to the cartridge mounting unit 100. The second shaft 220 may have a rotating-preventing structure like the first shaft 120. The second shaft 220 may have a quadrangular cross-section as the rotation-preventing structure.

The transducer holder 230 has a first side to hold the transducer 240, and is movable on the second shaft 220 along an extended direction of the second shaft 220. The transducer holder 230 may have a hole in which the second shaft 220 is inserted. The hole may have a rectangular shape corresponding to the cross-section shape of the second shaft 220. The first side of the transducer holder 230 may be extended to have a predetermined length from the connecting position of the shaft toward the cartridge mounting unit 100. Referring to FIG. 21, the transducer holder 230 may be provided with the second magnet 231 in a portion extended upward. The second magnet 231 may be disposed with its pole oriented upward so that magnetic density can increase in a direction toward the first magnet 131 of the cartridge mounting unit 100.

The transducer 240 may be configured to generate the ultrasound energy. The transducer 240 may be configured to focus the ultrasound energy in the tissue of the skin when a contact outside, i.e., the contact portion of the cartridge housing 210 is in contact with the skin. Therefore, it is possible to generate deep heat under the skin surface, and treat the tissue. Meanwhile, the widespread configuration may be employed as the configuration of the transducer 240.

Although the foregoing example shows that one first magnet 131 and one second magnet 231 are provided, combination of a plurality of magnets, of which poles are opposite to each other, may be provided as each of the first magnet 131 and the second magnet 231. In this case, coupling between the first magnet 131 and the second magnet 231 may be performed more accurately, thereby minimizing a position error in a horizontal direction.

Meanwhile, wiring may be provided to supply energy to the transducer 240. The wiring has a first side connected to the transducer 240, and a second side connected to the terminal of the first side of the cartridge housing 210. The terminal may be provided to penetrate the cartridge housing 210 and electrically connected to the outside of the housing. When the cartridge 200 is mounted to the cartridge mounting unit 100, the terminal may be electrically connected to the first side of the cartridge mounting unit 100 or the first side of the handpiece 10.

Meanwhile, an area of the cartridge housing 210, in which the terminal is installed to penetrate the cartridge housing 210, is sealed up to completely prevent the liquid medium from leakage. Therefore, it is possible to prevent the liquid medium from leaking out of the cartridge 200 when a user grips the handpiece 10 upside down or tilts the handpiece 10.

Meanwhile, although it is not shown, the cartridge mounting unit 100 may include a sensor to identify the position of the guide unit 130 and/or the transducer holder 230. The sensor may for example be provided as a position sensor to detect the position of the guide unit 130 and/or the transducer holder 230. Further, the sensor may be provided in the form of an encoder to detect a rotated angle of a motor and identify the position of the transducer 240 based on the amount of actuating the motor. Such a sensor may have a widespread configuration, and thus detailed descriptions thereof will be omitted.

Figure 23:
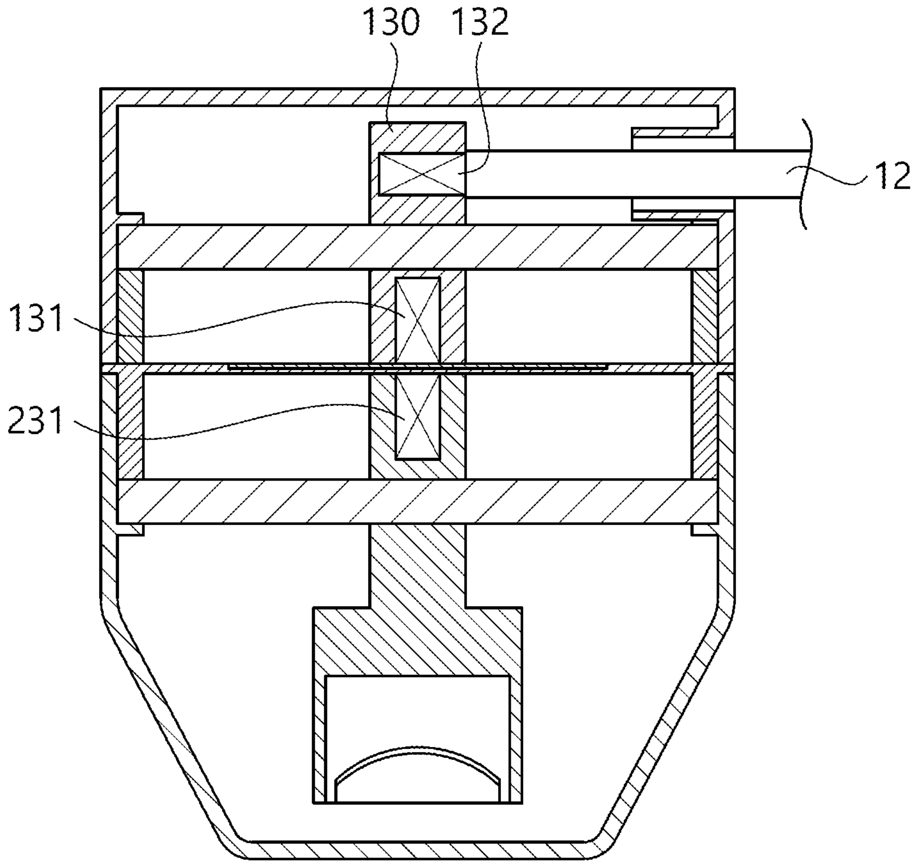
FIG. 23 illustrates operating states of adjusting a horizontal position of a transducer.

FIG. 23 illustrates operating states of adjusting a horizontal position of the transducer 240.

Referring to FIG. 23, the first magnet 131 and the second magnet 231 are coupled to each other, and adjusted in position under the condition that their positions in a horizontal direction are synchronized in FIG. 23. In this case, the guide unit 130 may be adjusted in position in the state that the actuation rod 12 inserted from the outside of the cartridge mounting unit 100 is in close contact with the holding magnet 132. The actuator provided in the handpiece 10 is driven by a control input to adjust the length of the actuation rod 12 to be inserted in the cartridge mounting unit 100.

The guide unit 130 may be passively adjusted in position on the first shaft 120 by the actuation rod 12. In this case, the movement of the guide unit 130 causes the position of the second magnet 231 coupling with the first magnet 131 to be adjusted by the magnetic attraction, thereby finally making the position of the transducer holder 230 be passively adjusted. On one hand, the guide unit 130 and the transducer holder 230 are moved leftward on FIG. 23 as the actuation rod 12 is inserted. On the other hand, when the actuation rod 12 is pulled out of the cartridge mounting unit 100, the holding magnet 132 being in close contact with the end portion of the actuation rod 12 is moved rightward on FIG. 23, thereby finally making the position of the transducer holder 230 be moved rightward.

With this structure, the position of the transducer 240 is moved based on magnetic force without contact, and therefore the skin treatment apparatus 1 using the high-intensity focused ultrasound operates while hermetically maintaining the liquid medium filled in the cartridge 200. Further, it is also possible to prevent liquid from leakage even while the cartridge 200 is mounted or unmounted.

As described above, the position of the transducer 240 is movable inside the cartridge 200, so that a user can enlarge the treatment area without moving the handpiece 10. In other words, when a user controls operations while the end portion of the cartridge 200 is in close contact with skin, the transducer 240 ultimately moves inside the cartridge 200 based on the actuation of the motor. In this case, it is possible to perform the treatment throughout a wide area because the ultrasound energy is transmitted during the position adjustment. In other words, the transducer 240 is movable inside the cartridge 200, and therefore the frequency of moving the handpiece 10, which is repetitively performed to change a treatment location, is reduced, thereby maximizing the convenience of use.

Below, operations of initializing the position of the transducer holder 230 when the cartridge 200 is mounted to the cartridge mounting unit 100 will be described with reference to FIGS. 24A to 24D.

FIGS. 24A, 24B, 24C and 24D illustrate operating states of initializing a position when the cartridge is mounted.

Figure 24A:
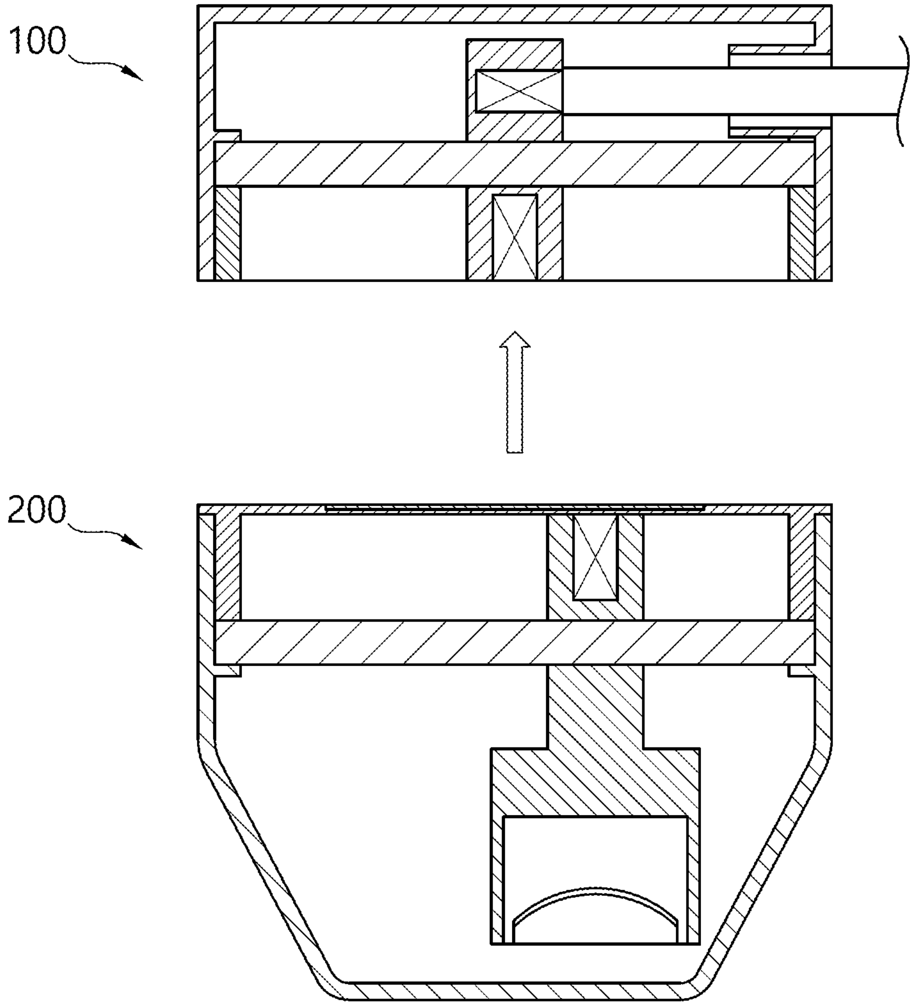
FIGS. 24A, 24B, 24C and 24D illustrate operating states of initializing a position when the cartridge is mounted.

Referring to FIG. 24A, the cartridge 200 is aligned with and disposed under the cartridge mounting unit 100.

Figure 24B:
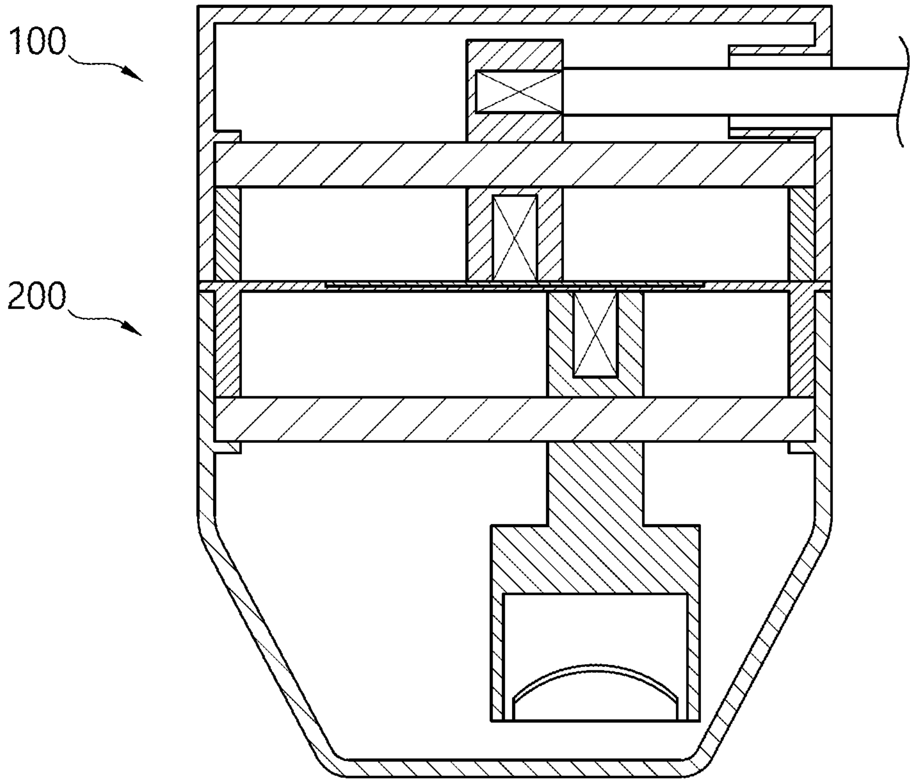

Referring to FIG. 24B, the cartridge 200 is then mounted to the cartridge mounting unit 100. In this case, the guide unit 130 and the holder of the cartridge 200 are a little distant from each other in a horizontal direction, and there is no movement based on magnetic force.

Figure 24C:
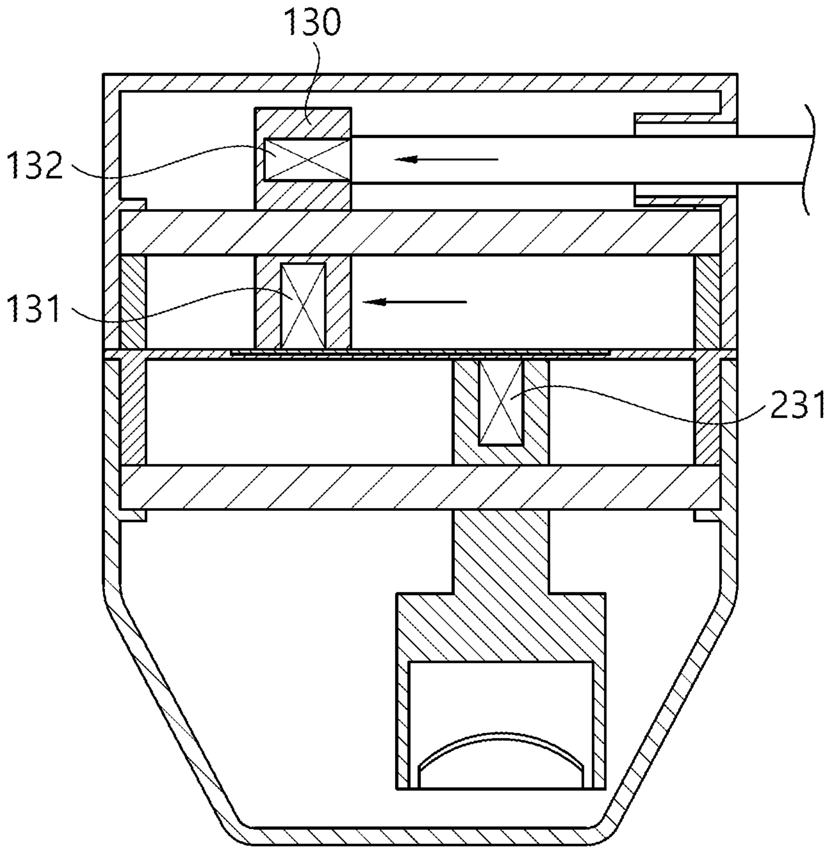

Referring to FIG. 24C, the controller then controls the actuator to move the guide unit 130 to the leftmost end within a movable range by the actuation rod 12.

Referring to FIG. 24C, in reverse to FIG. 24C, the controller then controls the actuator to move the guide unit 130 to the rightmost end within the movable range by the actuation rod 12.

Figure 24D:
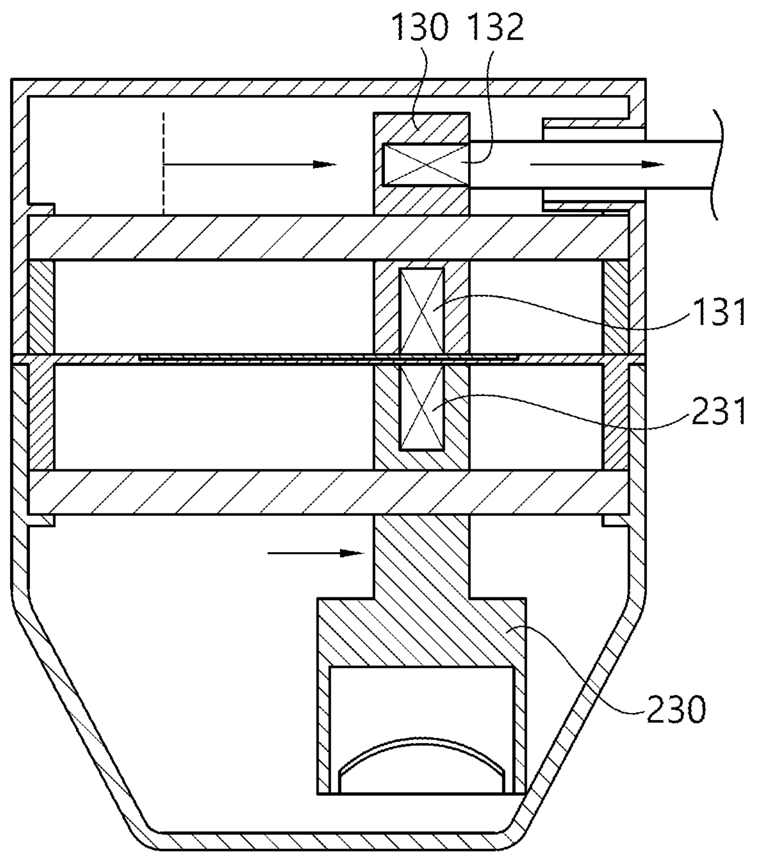

Based on the operations of the actuator 11 performed in FIGS. 24C and 24D, the guide unit 130 horizontally reciprocates a predetermined distance via a position where the transducer holder 230 is placed. As the guide unit 130 reciprocates the maximum stroke distance once, the first magnet 131 and the second magnet 231 are coupled, and the position of the guide unit 130 and the position of the transducer holder 230 are synchronized.

However, the order illustrated in FIGS. 24C and 24D is merely an example, and the guide unit 130 may move the maximum stroke distance in any order.

Meanwhile, when the position of the guide unit 130 and the position of the transducer holder 230 are synchronized, the position of the transducer 240 is ultimately adjusted by adjusting the position of the actuation rod 12 as described above with reference to FIG. 23.

Below, a control method of the skin treatment apparatus using the high-intensity focused ultrasound according to another embodiment of the disclosure will be described with reference to FIG. 25.

Figure 25:
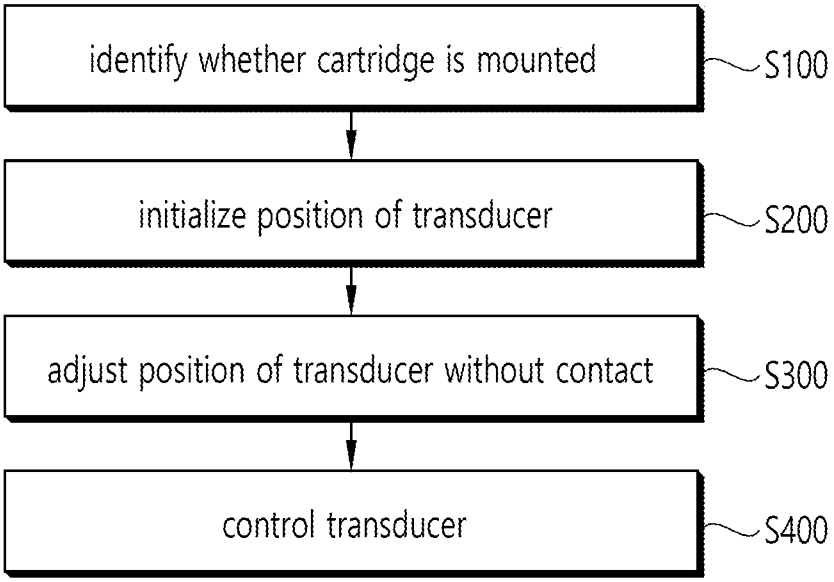
FIG. 25 is a flowchart showing a control method of a skin treatment apparatus using high-intensity focused ultrasound according to an eighth embodiment of the disclosure.

FIG. 25 is a flowchart showing a control method of a skin treatment apparatus using high-intensity focused ultrasound according to an eighth embodiment of the disclosure.

Referring to FIG. 25, the control method of the skin treatment apparatus using the high-intensity focused ultrasound according to the eighth embodiment of the disclosure may include operation S100 of identifying whether the cartridge is mounted, operation S200 of initializing the position of the transducer, operation S300 of adjusting the position of the transducer without contact, and operation S400 of controlling the transducer.

The operation S100 of identifying whether the cartridge is mounted or not refers to operation of identifying whether the cartridge including the transducer is mounted to the cartridge mounting unit. The cartridge may include electric terminals at the first side, and the cartridge mounting unit may include other terminals to be in contact with the electric terminals. Therefore, it may be identified based on detection of an electric signal whether the cartridge is mounted to the cartridge mounting unit. Besides this method, various conventional methods may be used to identify whether the cartridge is mounted or not. As an example of performing this operation, the cartridge mounting unit or the handpiece may include a button at a first side thereof, and the button may be pushed to generate an electric signal when the cartridge is mounted.

The operation S200 of initializing the position of the transducer refers to operation of synchronizing the position of the transducer inside the cartridge. The cartridge described above with reference to FIGS. 10 to 24D may be used, and sealed up with the transducer accommodated therein. By moving the magnet outside the cartridge to couple with the magnet inside the cartridge based on magnetic attraction, the position of the transducer is initialized. In this case, when the magnet reciprocates within the movable range inside the cartridge, the transducer holder placed at any position sticks to the magnet and is then passively moved as the magnet outside the cartridge is moved, thereby synchronously moving the position of the transducer.

The operation S300 of adjusting the position of the transducer without contact refers to operation of moving the magnet outside the cartridge in order to adjust the position of the transducer. When the position of the transducer is initialized, in other words, when the magnet outside the cartridge and the position of the transducer are synchronized, it is possible to adjust the position of the transducer without contact by adjusting the position of the magnet. In this case, the position of the transducer and/or the magnet, which is detected by a separately provided sensor, may be fed back to position control.

The operation S400 of controlling the transducer refers to operation of controlling the ultrasound energy generated by the transducer. The ultrasound energy generated by the transducer may be focused outside the cartridge. This operation of controlling the transducer may further include operation of controlling a focal position of the transducer. When the focal position of the transducer is controlled, it is possible to adjust depth in which deep heat is generated, and it is thus possible to adjust the treatment location in a depth direction. The operation of controlling a focal distance of the transducer may include operation of adjusting the position of the transducer in a vertical direction, thereby adjusting the focal position at which the ultrasound is focused.

Meanwhile, the operation of controlling the transducer and the operation of adjusting the position of the transducer without contact may be alternately or simultaneously performed to thereby appropriately and uniformly treat the wide area.

Meanwhile, the skin treatment apparatus using the high-intensity focused ultrasound, used in this control method, may use the skin treatment apparatus using the high-intensity focused ultrasound described with reference to FIG. 10 to FIG. 24D.

In the skin treatment apparatus using the high-intensity focused ultrasound, the control method thereof, and the skin treatment method using the same, which are described above according to the disclosure, it is possible to shorten treatment time because a wide area is first heated and a target position is then heated to be remodeled when tissue is heated. Further, it is possible to have an improved recovering effect because activity of cells is enhanced.

As described above, the skin treatment apparatus using high-intensity focused ultrasound according to the disclosure and the method of controlling the same have effects on securing operation stability because a transducer is movable while independent environments inside a cartridge are maintained by a simple structure.

Further, the transducer is movable as it is automatically coupled when the cartridge is mounted, thereby having an effect on improving convenience.

With a skin treatment apparatus using high-intensity focused ultrasound according to the disclosure, a control method thereof, and a skin treatment method using the same, it is possible to shorten treatment time because a wide area is first heated and a target position is then heated to be remodeled when tissue is heated. Further, it is possible to have an improved recovering effect because activity of cells is enhanced.

Further, a skin treatment apparatus using high-intensity focused ultrasound according to the disclosure and a method of controlling the same have effects on securing operation stability because a transducer is movable while independent environments inside a cartridge are maintained by a simple structure. In addition, the transducer is movable as it is automatically coupled when the cartridge is mounted, thereby having an effect on improving convenience.

Although a few embodiments have been shown and described, it will be appreciated by those skilled in the art that changes may be made in these embodiments without departing from the principles and spirit of the invention, the scope of which is defined in the appended claims and their equivalents.

The invention claimed is:

1. A skin treatment apparatus using high-intensity focused ultrasound, comprising:
- a handpiece;
- a cartridge provided at an end portion of the handpiece and facing toward a first side; and
- a cartridge mounting unit configured to couple the cartridge to the handpiece,
- wherein the cartridge comprises:
  - a transducer configured to generate ultrasound to be focused in a treatment area through a tip of the cartridge; and
  - at least one electrode provided in the tip and configured to transmit radio frequency (RF) energy to the treatment area,
- wherein the at least one electrode is configured to heat the treatment area at a first temperature to improve an efficiency of transmitting the ultrasound, wherein the apparatus further comprises a controller configured to transmit the RF energy to the at least one electrode without transmitting the ultrasound to be focused in the treatment area until a temperature of the treatment area reaches the first temperature, and the first temperature is below a temperature at which tissue denaturation occurs, wherein the controller is further configured to, after the transmitting the RF energy has been complete, transmit the ultrasound to the treatment area without transmitting the RF energy until the temperature of the treatment area increases to a second temperature higher than the first temperature, and the second temperature comprises a temperature at which coagulation occurs in the treatment area, wherein the cartridge mounting unit includes a first magnet and the cartridge further comprises a second magnet, the first magnet and the second magnet are magnetically coupled to each other to make the transducer reciprocate in a specific direction, and the first magnet and the second magnet are spaced apart from each other by a separation film that prevents liquid leakage, wherein the cartridge mounting unit further includes a mounting-unit housing, a first shaft, a guide unit, and a holding magnet, wherein the first shaft has opposite ends connected to the mounting-unit housing, the guide unit is configured to reciprocate on the first shaft in the specific direction, the first magnet is provided in a lower portion of the guide unit, and the holding magnet is provided in an upper portion of the guide unit, wherein the cartridge further comprises a cartridge housing, a second shaft, and a transducer holder, and wherein the second shaft is disposed in the cartridge housing, and the transducer holder is configured to move on the second shaft in the specific direction and is provided with the second magnet.

2. The skin treatment apparatus according to claim 1, wherein the electrode is adjacent to an ultrasound passing area in the tip.

3. The skin treatment apparatus according to claim 2, wherein the electrode comprises a plurality of electrodes, and comprises a bipolar electrode.

4. The skin treatment apparatus according to claim 3, wherein the transducer is configured to be adjusted in position inside the cartridge.

5. The skin treatment apparatus according to claim 4, wherein the cartridge further includes an actuator configured to adjust the position of the transducer inside the cartridge by making the transducer reciprocate in a specific direction.

6. The skin treatment apparatus according to claim 5, wherein the specific direction is parallel to the ultrasound passing area.

7. The skin treatment apparatus according to claim 4, wherein the transducer is configured to reciprocate between the plurality of electrodes.

8. The skin treatment apparatus according to claim 4, wherein the RF energy transmitted heats a first area and the ultrasound to be focused by the transducer heats a second area, and wherein the transducer is configured to move inside the cartridge such that the second area is formed within the first area.

9. The skin treatment apparatus according to claim 1, wherein the first temperature is 45° C., and the second temperature is 70° C.

10. A control method of a skin treatment apparatus using high-intensity focused ultrasound, the control method comprising:

transmitting radio frequency (RF) energy to at least one electrode provided in a tip of a cartridge of a handpiece; and transmitting energy to a transducer provided in the cartridge to generate ultrasound, wherein the transmitting the RF energy is performed without performing the transmitting energy to generate the ultrasound until a temperature of a treatment area reaches a first temperature that is below a temperature at which tissue denaturation occurs, and, wherein, after the transmitting the RF energy has been complete, the transmitting the energy to generate the ultrasound is performed without transmitting the RF energy until the temperature of the treatment area increases to a second temperature higher than the first temperature, and the second temperature comprises a temperature at which coagulation occurs in the treatment area, wherein the skin treatment apparatus comprises:

the handpiece;

the cartridge provided at an end portion of the handpiece and facing toward a first side; and a cartridge mounting unit configured to couple the cartridge to the handpiece, wherein the cartridge comprises:

the transducer configured to generate ultrasound to be focused in a treatment area through a tip of the cartridge; and the at least one electrode provided in the tip and configured to transmit radio frequency (RF) energy to the treatment area, wherein the at least one electrode is configured to heat the treatment area at a first temperature to improve an efficiency of transmitting the ultrasound, wherein the apparatus further comprises a controller configured to transmit the RF energy to the at least one electrode without transmitting the ultrasound to be focused in the treatment area until a temperature of the treatment area reaches the first temperature, and the first temperature is below a temperature at which tissue denaturation occurs, wherein the controller is further configured to, after the transmitting the RF energy has been complete, transmit the ultrasound to the treatment area without transmitting the RF energy until the temperature of the treatment area increases to a second temperature higher than the first temperature, and the second temperature comprises a temperature at which coagulation occurs in the treatment area, wherein the cartridge mounting unit includes a first magnet and the cartridge further comprises a second magnet, the first magnet and the second magnet are magnetically coupled to each other to make the transducer reciprocate in a specific direction, and the first magnet and the second magnet are spaced apart from each other by a separation film that prevents liquid leakage, wherein the cartridge mounting unit further includes a mounting-unit housing, a first shaft, a guide unit, and a holding magnet, wherein the first shaft has opposite ends connected to the mounting-unit housing, the guide unit is configured to reciprocate on the first shaft in the specific direction, the first magnet is provided in a lower portion of the guide unit, and the holding magnet is provided in an upper portion of the guide unit, wherein the cartridge further comprises a cartridge housing, a second shaft, and a transducer holder, and wherein the second shaft is disposed in the cartridge housing, and the transducer holder is configured to move on the second shaft in the specific direction and is provided with the second magnet.

11. The control method according to claim 10, further comprising identifying whether the temperature of the treatment area reaches the first temperature based on a value detected by a sensor after the transmitting the RF energy.

12. The control method according to claim 11, wherein the transmitting the RF energy to the electrode comprises using a plurality of electrodes disposed around and adjacent to an ultrasound passing area in which the ultrasound generated by the transducer passes through the cartridge.

13. The control method according to claim 12, wherein the transmitting the RF energy to the electrode is performed by transmitting bipolar RF energy.

* * * * *